US009615821B2

(12) United States Patent
Sullivan

(10) Patent No.: US 9,615,821 B2
(45) Date of Patent: Apr. 11, 2017

(54) TENSIONABLE KNOTLESS ANCHOR SYSTEMS AND METHODS OF TISSUE REPAIR

(71) Applicant: Arthrex, Inc., Naples, FL (US)

(72) Inventor: Derek C. Sullivan, Naples, FL (US)

(73) Assignee: Arthrex, Inc., Naples, FL (US)

( * ) Notice: Subject to any disclaimer, the term of this patent is extended or adjusted under 35 U.S.C. 154(b) by 649 days.

(21) Appl. No.: 13/709,138

(22) Filed: Dec. 10, 2012

(65) Prior Publication Data
US 2013/0165972 A1    Jun. 27, 2013

Related U.S. Application Data

(60) Provisional application No. 61/569,041, filed on Dec. 9, 2011.

(51) Int. Cl.
A61B 17/04    (2006.01)
A61B 17/06    (2006.01)

(52) U.S. Cl.
CPC .. *A61B 17/0401* (2013.01); *A61B 2017/0403* (2013.01); *A61B 2017/0412* (2013.01); *A61B 2017/0445* (2013.01); *A61B 2017/0448* (2013.01); *A61B 2017/0458* (2013.01); *A61B 2017/0475* (2013.01); *A61B 2017/06185* (2013.01)

(58) Field of Classification Search
CPC ........ A61B 17/0401; A61B 2017/0409; A61B 2017/0412; A61B 2017/0414; A61B 2017/0445; A61B 2017/0446; A61B 2017/0448; A61B 2017/045; A61B 2017/0451; A61B 2017/0458; A61B 2017/0459; A61B 2017/0462; A61B 2017/0464; A61B 2017/0466; A61B 2017/0469; A61B 2017/0474; A61B 2017/0477; A61B 2017/0475; A61B 2017/0485; A61B 2017/0496; A61B 2017/0403; A61B 2017/06185; A61F 2/0811; A61F 2002/0888; A61F 2002/0852
See application file for complete search history.

(56) References Cited

U.S. PATENT DOCUMENTS

| | | | |
|---|---|---|---|
| 3,176,316 A | 4/1965 | Bodell | |
| 4,187,558 A | 2/1980 | Dahlen et al. | |
| 4,301,551 A | 11/1981 | Dore et al. | |
| 4,400,833 A | 8/1983 | Kurland | |
| 4,776,851 A | 10/1988 | Bruchman et al. | |

(Continued)

FOREIGN PATENT DOCUMENTS

| | | |
|---|---|---|
| DE | 299 10 202 U1 | 9/1999 |
| DE | 201 01 791 U1 | 6/2001 |

(Continued)

*Primary Examiner* — Jocelin Tanner
(74) *Attorney, Agent, or Firm* — Blank Rome LLP

(57) ABSTRACT

Systems and methods for soft tissue to bone repairs, without knot tying. The soft tissue repair systems include self-cinching constructs with splices and loops that are preloaded onto modified knotless anchors (for example, swivel and/or screw-in suture anchors and/or push-in suture anchors with a distal eyelet) to position the self-locking, adjustable construct at the repair site. The systems allow for knotless tensioning of the tissue after the knotless anchors have been implanted.

6 Claims, 22 Drawing Sheets

(56) References Cited

U.S. PATENT DOCUMENTS

| | | |
|---|---|---|
| 4,790,850 A | 12/1988 | Dunn et al. |
| 4,792,336 A | 12/1988 | Hlavacek et al. |
| 4,851,005 A | 7/1989 | Hunt et al. |
| 4,863,471 A | 9/1989 | Mansat |
| 4,917,700 A | 4/1990 | Aikins |
| 4,932,972 A | 6/1990 | Dunn et al. |
| 5,024,669 A | 6/1991 | Peterson et al. |
| 5,026,398 A | 6/1991 | May et al. |
| 5,129,902 A | 7/1992 | Goble et al. |
| 5,171,274 A | 12/1992 | Fluckiger et al. |
| 5,211,647 A | 5/1993 | Schmieding |
| 5,217,495 A | 6/1993 | Kaplan et al. |
| 5,263,984 A | 11/1993 | Li et al. |
| 5,266,075 A | 11/1993 | Clark et al. |
| 5,306,301 A | 4/1994 | Graf et al. |
| 5,320,626 A | 6/1994 | Schmieding |
| 5,397,357 A | 3/1995 | Schmieding et al. |
| 5,562,669 A | 10/1996 | McGuire |
| 5,575,819 A | 11/1996 | Amis |
| 5,628,756 A | 5/1997 | Barker et al. |
| 5,643,266 A | 7/1997 | Li |
| 5,645,588 A | 7/1997 | Graf et al. |
| 5,931,869 A | 8/1999 | Boucher et al. |
| 5,961,520 A | 10/1999 | Beck et al. |
| 5,964,764 A | 10/1999 | West, Jr. et al. |
| 6,056,752 A | 5/2000 | Roger |
| 6,099,530 A | 8/2000 | Simonian et al. |
| 6,099,568 A | 8/2000 | Simonian et al. |
| 6,110,207 A | 8/2000 | Eichhorn et al. |
| 6,159,234 A | 12/2000 | Bonutti et al. |
| 6,193,754 B1 | 2/2001 | Seedhom |
| 6,203,572 B1 | 3/2001 | Johnson et al. |
| 6,283,996 B1 | 9/2001 | Chervitz et al. |
| 6,296,659 B1 | 10/2001 | Foerster |
| 6,325,804 B1 | 12/2001 | Wenstrom et al. |
| 6,517,578 B2 | 2/2003 | Hein |
| 6,533,802 B2 | 3/2003 | Bojarski et al. |
| 7,097,654 B1 | 8/2006 | Freedland |
| 7,494,506 B2 | 2/2009 | Brulez et al. |
| 7,686,838 B2 | 3/2010 | Wolf et al. |
| 7,749,250 B2 | 7/2010 | Stone et al. |
| 7,776,039 B2 | 8/2010 | Bernstein et al. |
| 7,819,898 B2 | 10/2010 | Stone et al. |
| 7,828,855 B2 | 11/2010 | Ellis et al. |
| 7,875,057 B2 | 1/2011 | Cook et al. |
| 7,905,903 B2 | 3/2011 | Stone et al. |
| 7,914,539 B2 | 3/2011 | Stone et al. |
| 8,109,965 B2 | 2/2012 | Stone et al. |
| 8,118,836 B2 | 2/2012 | Denham et al. |
| 8,162,997 B2 | 4/2012 | Struhl |
| 8,206,446 B1 | 6/2012 | Montgomery |
| 8,231,654 B2 | 7/2012 | Kaiser et al. |
| 2001/0041938 A1 | 11/2001 | Hein |
| 2002/0161439 A1 | 10/2002 | Strobel et al. |
| 2003/0114929 A1 | 6/2003 | Knudsen et al. |
| 2004/0015171 A1 | 1/2004 | Bojarski et al. |
| 2004/0059415 A1 | 3/2004 | Schmieding |
| 2004/0073306 A1 | 4/2004 | Eichhorn et al. |
| 2004/0243235 A1 | 12/2004 | Goh et al. |
| 2004/0267360 A1 | 12/2004 | Huber |
| 2005/0004670 A1 | 1/2005 | Gebhardt et al. |
| 2005/0033363 A1 | 2/2005 | Bojarski et al. |
| 2005/0065533 A1 | 3/2005 | Magen et al. |
| 2005/0070906 A1 | 3/2005 | Clark et al. |
| 2005/0137704 A1 | 6/2005 | Steenlage |
| 2005/0149187 A1 | 7/2005 | Clark et al. |
| 2005/0171603 A1 | 8/2005 | Justin et al. |
| 2005/0203623 A1 | 9/2005 | Steiner et al. |
| 2005/0261766 A1 | 11/2005 | Chervitz et al. |
| 2006/0004364 A1 | 1/2006 | Green et al. |
| 2006/0067971 A1 | 3/2006 | Story et al. |
| 2006/0095130 A1 | 5/2006 | Caborn et al. |
| 2006/0142769 A1 | 6/2006 | Collette |
| 2006/0265064 A1 | 11/2006 | Re et al. |
| 2007/0021839 A1 | 1/2007 | Lowe |
| 2007/0083236 A1* | 4/2007 | Sikora et al. ................ 606/232 |
| 2007/0118217 A1 | 5/2007 | Brulez et al. |
| 2007/0162123 A1 | 7/2007 | Whittaker et al. |
| 2007/0162125 A1 | 7/2007 | LeBeau et al. |
| 2007/0179531 A1 | 8/2007 | Thornes |
| 2007/0225805 A1 | 9/2007 | Schmieding |
| 2007/0239209 A1 | 10/2007 | Fallman |
| 2007/0239275 A1 | 10/2007 | Willobee |
| 2007/0250163 A1 | 10/2007 | Cassani |
| 2007/0270857 A1 | 11/2007 | Lombardo et al. |
| 2008/0046009 A1 | 2/2008 | Albertorio et al. |
| 2008/0051835 A1* | 2/2008 | Mazzocca et al. ............ 606/222 |
| 2008/0065114 A1* | 3/2008 | Stone et al. .................. 606/139 |
| 2008/0103528 A1* | 5/2008 | Zirps .................. A61B 17/0401 |
| | | 606/232 |
| 2008/0177302 A1 | 7/2008 | Shurnas |
| 2008/0188935 A1 | 8/2008 | Saylor et al. |
| 2008/0188936 A1 | 8/2008 | Ball et al. |
| 2008/0208252 A1 | 8/2008 | Holmes |
| 2008/0215150 A1 | 9/2008 | Koob et al. |
| 2008/0228271 A1 | 9/2008 | Stone et al. |
| 2008/0234819 A1 | 9/2008 | Schmieding et al. |
| 2008/0243248 A1 | 10/2008 | Stone et al. |
| 2008/0255613 A1* | 10/2008 | Kaiser et al. ................. 606/232 |
| 2008/0275553 A1 | 11/2008 | Wolf et al. |
| 2008/0275554 A1 | 11/2008 | Iannarone et al. |
| 2008/0300683 A1 | 12/2008 | Altman et al. |
| 2008/0312689 A1* | 12/2008 | Denham et al. .............. 606/232 |
| 2009/0018654 A1 | 1/2009 | Schmieding et al. |
| 2009/0030516 A1 | 1/2009 | Imbert |
| 2009/0054982 A1 | 2/2009 | Cimino |
| 2009/0062854 A1* | 3/2009 | Kaiser et al. ................. 606/232 |
| 2009/0082805 A1* | 3/2009 | Kaiser ............... A61B 17/0401 |
| | | 606/228 |
| 2009/0187244 A1 | 7/2009 | Dross |
| 2009/0216326 A1 | 8/2009 | Hirpara et al. |
| 2009/0228017 A1 | 9/2009 | Collins |
| 2009/0234451 A1 | 9/2009 | Manderson |
| 2009/0265003 A1 | 10/2009 | Re et al. |
| 2009/0275950 A1 | 11/2009 | Sterrett et al. |
| 2009/0306776 A1 | 12/2009 | Murray |
| 2009/0306784 A1 | 12/2009 | Blum |
| 2009/0312776 A1 | 12/2009 | Kaiser et al. |
| 2010/0049258 A1 | 2/2010 | Dougherty |
| 2010/0049319 A1 | 2/2010 | Dougherty |
| 2010/0100182 A1 | 4/2010 | Barnes et al. |
| 2010/0145384 A1 | 6/2010 | Stone et al. |
| 2010/0145448 A1 | 6/2010 | Montes De Oca Balderas et al. |
| 2010/0211075 A1 | 8/2010 | Stone |
| 2010/0211173 A1 | 8/2010 | Bardos et al. |
| 2010/0249930 A1 | 9/2010 | Myers |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0274355 A1 | 10/2010 | McGuire et al. |
| 2010/0274356 A1 | 10/2010 | Fening et al. |
| 2010/0292792 A1 | 11/2010 | Stone et al. |
| 2010/0305709 A1 | 12/2010 | Metzger et al. |
| 2010/0312341 A1 | 12/2010 | Kaiser et al. |
| 2010/0318188 A1 | 12/2010 | Linares |
| 2010/0324676 A1 | 12/2010 | Albertorio et al. |
| 2010/0331975 A1 | 12/2010 | Nissan et al. |
| 2011/0040380 A1 | 2/2011 | Schmieding et al. |
| 2011/0046734 A1 | 2/2011 | Tobis et al. |
| 2011/0054609 A1 | 3/2011 | Cook et al. |
| 2011/0087284 A1 | 4/2011 | Stone et al. |
| 2011/0098727 A1 | 4/2011 | Kaiser et al. |
| 2011/0112640 A1 | 5/2011 | Amis et al. |
| 2011/0112641 A1 | 5/2011 | Justin et al. |
| 2011/0118838 A1 | 5/2011 | Delli-Santi et al. |
| 2011/0137416 A1 | 6/2011 | Myers |
| 2011/0184227 A1 | 7/2011 | Altman et al. |
| 2011/0196432 A1 | 8/2011 | Griffis, III |
| 2011/0196490 A1 | 8/2011 | Gadikota et al. |
| 2011/0218625 A1 | 9/2011 | Berelsman et al. |
| 2011/0238179 A1 | 9/2011 | Laurencin et al. |
| 2011/0270278 A1 | 11/2011 | Overes et al. |
| 2011/0276137 A1 | 11/2011 | Seedhom et al. |
| 2011/0288635 A1 | 11/2011 | Miller et al. |

(56) References Cited

U.S. PATENT DOCUMENTS

| | | |
|---|---|---|
| 2011/0301707 A1 | 12/2011 | Buskirk et al. |
| 2011/0301708 A1 | 12/2011 | Stone et al. |
| 2012/0046746 A1 | 2/2012 | Konicek |
| 2012/0046747 A1 | 2/2012 | Justin et al. |
| 2012/0053630 A1 | 3/2012 | Denham et al. |
| 2012/0065732 A1 | 3/2012 | Roller et al. |
| 2012/0089143 A1 | 4/2012 | Martin et al. |
| 2012/0109299 A1 | 5/2012 | Li et al. |
| 2012/0123474 A1 | 5/2012 | Zajac et al. |
| 2012/0123541 A1 | 5/2012 | Albertorio et al. |
| 2012/0130423 A1* | 5/2012 | Sengun .............. A61B 17/0401 606/232 |
| 2012/0150297 A1 | 6/2012 | Denham et al. |
| 2012/0165864 A1* | 6/2012 | Hernandez ......... A61B 17/0401 606/232 |
| 2012/0165938 A1 | 6/2012 | Denham et al. |
| 2012/0197271 A1 | 8/2012 | Astorino et al. |
| 2012/0296345 A1 | 11/2012 | Wack et al. |
| 2013/0023928 A1 | 1/2013 | Dreyfuss |
| 2013/0023929 A1 | 1/2013 | Sullivan et al. |
| 2013/0103080 A1* | 4/2013 | Hernandez ......... A61B 17/0401 606/232 |

FOREIGN PATENT DOCUMENTS

| | | |
|---|---|---|
| EP | 0 440 991 A1 | 8/1991 |
| EP | 1 108 401 A1 | 6/2001 |
| EP | 1 707 127 A1 | 10/2006 |
| WO | WO 2007/002561 A1 | 1/2007 |
| WO | WO 2008/091690 A1 | 7/2008 |

\* cited by examiner

TENSIONABLE KNOTLESS ANCHOR SYSTEMS AND METHODS OF TISSUE REPAIR

CROSS-REFERENCE TO RELATED APPLICATIONS

This application claims the benefit of U.S. Provisional Application No. 61/569,041, filed Dec. 9, 2011, the disclosure of which is incorporated by reference in its entirety herein.

FIELD OF THE INVENTION

The present invention relates to methods and instruments for fixation of sutures and tissue to bone.

BACKGROUND OF THE INVENTION

When soft tissue such as a ligament or a tendon becomes detached from a bone, surgery is usually required to reattach or reconstruct the tissue. Often, a tissue graft is attached to the bone to facilitate regrowth and permanent attachment. Techniques and devices that have been developed generally involve tying the soft tissue with suture to an anchor or a hole provided in the bone tissue. Knotless suture anchors, such as the two piece Arthrex PushLock® anchor, disclosed in U.S. Pat. No. 7,329,272, have been developed to facilitate tissue fixation to bone.

It would be desirable to provide a knotless suture anchor system which has a design that allows tensioning of the tissue (particularly rotator cuff) after implantation of the suture anchors. Also needed is an improved technology for knotless fixation of the rotator cuff with easier suture management and increased tensioning of the rotator cuff.

SUMMARY OF THE INVENTION

The instruments and methods of the present invention provide knotless, adjustable anchor systems that allow for knotless tensioning of tissue (such as the rotator cuff) after anchor implantation. The knotless, adjustable anchor systems include knotless anchors (for example, swivel and/or screw-in suture anchors and/or push-in suture anchors with a distal eyelet) that are modified to carry a self-locking, adjustable construct (for example, a suture assembly with a spliced suture loop) and to position the self-locking, adjustable construct at the repair site. The systems allow for knotless tensioning of the tissue after the knotless anchors have been implanted.

Other features and advantages of the present invention will become apparent from the following description of exemplary embodiments of the invention described with reference to the accompanying drawings.

DETAILED DESCRIPTION OF THE PREFERRED EMBODIMENTS

Figure 1:
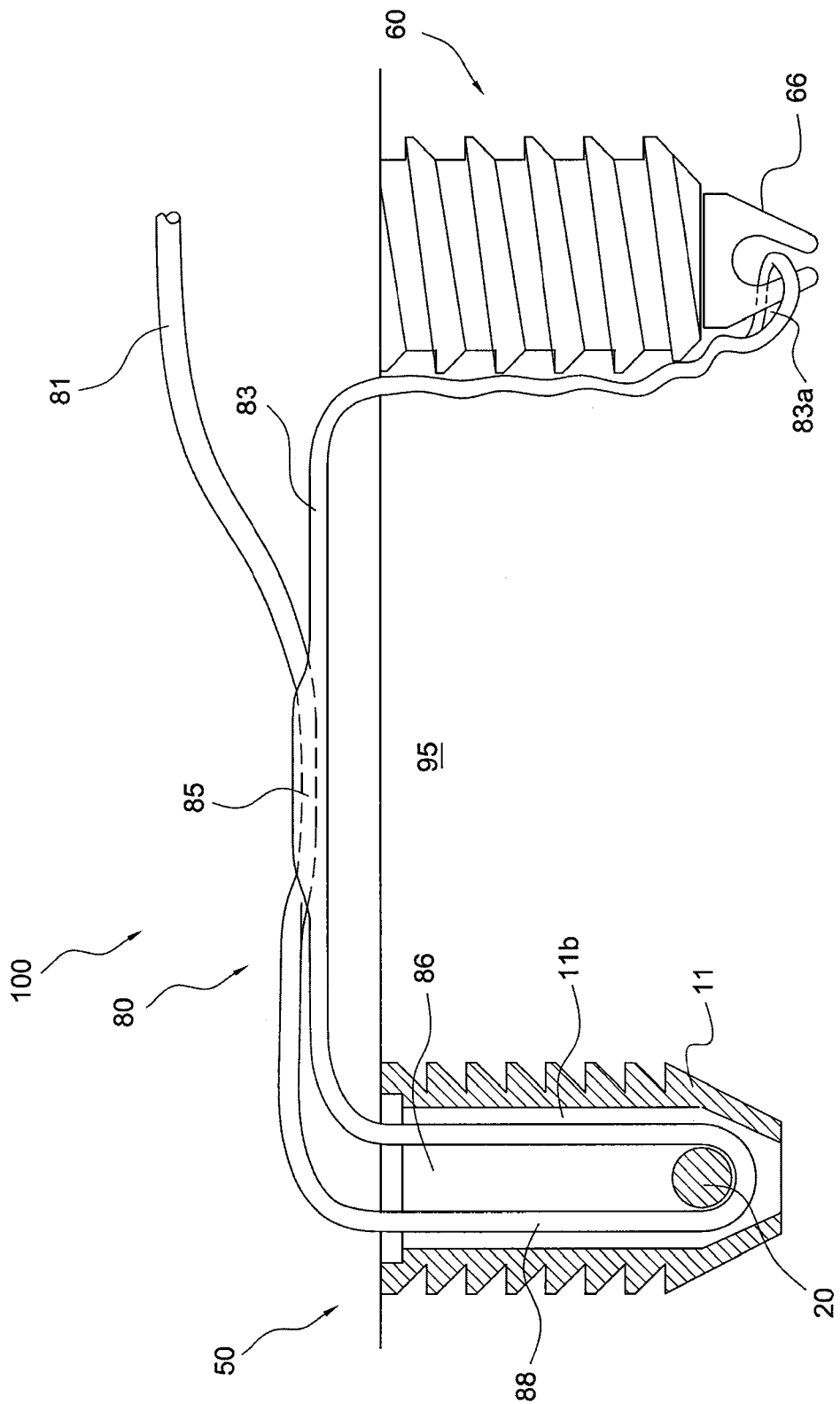
FIGS. 1 and 2 illustrate schematic views of a knotless, adjustable, tensionable anchor system according to an exemplary embodiment of the present invention.

The present invention provides surgical constructs, systems and techniques for knotless soft tissue repair and fixation, such as fixation of soft tissue (ligament, tendon, graft, etc.) to bone, and for the tensioning of the tissue (for example, rotator cuff) after anchor implantation.

The surgical constructs comprise fixation devices (tensionable knotless anchors) that are inserted into bone with tensionable adjustable constructs attached to (pre-loaded onto) the fixation devices and that are self-cinching. The tensionable knotless construct is formed of a flexible strand provided with a splice formed within the strand, a spliced adjustable loop, and a free end. The splice may be formed within the body or outside the body of the fixation device. Subsequent to the insertion of the fixation devices within the bone (and subsequent to attachment to soft tissue to be repaired or fixated), the knotless self-locking mechanism of the tensionable construct allows the user (for example, the surgeon) to control the tension of the strand on the soft tissue to be attached to bone.

In an exemplary embodiment, a first-type surgical construct of the present invention comprises a fixation device (a suture anchor) with an attached (pre-loaded) tensionable construct formed of a flexible strand with a free end, a spliced adjustable loop and a fixed end in the form of a fixed loop. The fixed loop is attached to another fixation device. Other embodiments of this first-type construct include: (i) replacing the fixed loop with a knot that is captured by a closed eyelet of another fixation device (for example, in an eyelet of a SwiveLock® anchor); or (ii) eliminating the fixed loop and replacing it with just a free end of the suture that has been spliced, the free end being inserted into the closed eyelet of another fixation device (for example, a SwiveLock® anchor).

In another exemplary embodiment, a second-type surgical construct comprises a fixation device (a suture anchor) with an attached (pre-loaded) tensionable construct formed of a flexible strand with a free end, a spliced adjustable loop (located within the body of the fixation device), and a knotted fixed end or insert molded fixed end. A fixed loop (second loop) is attached to the spliced adjustable loop for further attachment to another fixation device (for example, being captured by an open eyelet of a SwiveLock® anchor). The knotted end (fixed end) is located on the fixation device (suture anchor), allowing the splice to be contained within the anchor body and allowing the two fixation devices to be placed closer together. With this exemplary type of construct, the second fixation device may be any type of fixation device, for example, swivel and/or screw-in suture anchors and/or push-in suture anchors, or even staples or similar devices. The second loop (fixed loop) in this construct is acting like a pulley or pivot point when it is attached to the second fixation device. Other embodiments of this second-type construct include: (i) replacing the second loop with a separate free suture used with a closed eyelet SwiveLock® anchor, so that the free suture is passed through the adjustable loop and then captured by the closed eyelet of the SwiveLock® anchor and positioned to keep the adjustable loop above the second anchor; or (ii) replacing the second loop with a free suture with one or more knots (for example, two knots located at a set distance apart from each other), passing the free suture through the adjustable loop and capturing the knots with a closed eyelet of the SwiveLock® anchor; or (iii) eliminating the second loop altogether and capturing the spliced adjustable loop with another fixation device (such as a staple, for example, or a modified SwiveLock® anchor that allows passing of the adjustable loop through a cannulation of the anchor).

The present invention also provides methods of soft tissue repair which do not require tying of knots and allow adjustment of both the tension of the suture and the location of the tissue with respect to the bone. An exemplary method of the present invention comprises inter alia the steps of: (i) providing a surgical construct comprising a fixation device (for example, an anchor) with an adjustable, tensionable construct attached to (pre-loaded onto) the fixation device, the knotless tensionable construct including a flexible strand with a splice, a spliced adjustable loop, and a free end; (ii) inserting the fixation device with the attached (pre-loaded) knotless tensionable construct at a first location into bone; (iii) further securing the flexible strand at a second location; and (iv) pulling on the free end to tension the final construct.

Another exemplary method of the present invention comprises inter alia the steps of: (i) providing a surgical construct comprising a fixation device (for example, an anchor) with an adjustable, tensionable construct attached to (pre-loaded onto) the fixation device, the knotless tensionable construct including a flexible strand with a splice formed within the flexible strand, a spliced adjustable loop, a free end and a fixed end in the form of a fixed loop; (ii) inserting the fixation device with the attached (pre-loaded) knotless tensionable construct into bone; (iii) passing the flexible strand around or through tissue to be fixated (or reattached) to bone; (iv) subsequently, attaching the fixed loop to another fixation device (a second fixation device); (v) securing the second fixation device (with the attached fixed loop) to or into bone; and (vi) pulling on the free end to allow the soft tissue to achieve the desired location relative to the bone, and to allow proper tensioning of the final construct. The fixed loop of the construct of this exemplary method may be replaced by a knot that is captured by a closed eyelet of the second fixation device (for example, by a closed eyelet of a SwiveLock® anchor); or it may be replaced with just a free end of the suture that has been spliced, the free end being inserted into the closed eyelet of the second fixation device (for example, the closed eyelet of a SwiveLock® anchor).

Another exemplary method of the present invention comprises inter alia the steps of: (i) providing a surgical construct comprising a fixation device (for example, an anchor) with an adjustable, tensionable construct attached to (pre-loaded onto) the fixation device, the knotless tensionable construct including a flexible strand with a splice, a spliced adjustable loop, a free end and a knotted fixed end (or an insert molded fixed end), the spliced adjustable end further including a fixed loop attached to the spliced construct; (ii) inserting the fixation device with the attached (pre-loaded) knotless tensionable construct into bone; (iii) passing the flexible strand around or through tissue to be fixated (or reattached) to bone; (iv) subsequently, capturing the fixed loop with another (second) fixation device; (v) inserting the second fixation device (with the captured fixed loop) into bone; and (vi) pulling on the free end to allow the soft tissue to achieve the desired location relative to the bone and to allow proper tensioning of the final construct. The fixed loop of the construct of this exemplary method may be replaced by a separate free suture used with a closed eyelet of the second fixation device (for example, a closed eyelet of a SwiveLock® anchor), so that the free suture is passed through the adjustable loop and then captured by the closed eyelet of the SwiveLock® anchor and positioned to keep the adjustable loop above the second anchor; or (ii) it may be replaced with a free suture with one or more knots (for example, two knots located at a set distance apart from each other), passing the free suture through the adjustable loop and capturing the knots with a closed eyelet of the SwiveLock® anchor; or (iii) it may be eliminated altogether to allow the spliced adjustable loop to be captured with the second fixation device (such as a staple, for example, or a modified SwiveLock® anchor that allows passing of the adjustable loop through a cannulation of the anchor).

Another exemplary method of the present invention comprises inter alia the steps of: (i) providing a surgical construct comprising a first fixation device (for example, an anchor) pre-loaded with a tensionable construct, the tensionable construct consisting of a flexible strand (for example, suture) extending through the body of the fixation device, the flexible strand consisting of a free end, a knotted fixed end or an insert molded fixed end, and a splice with a spliced adjustable loop, the splice being located within the body of the first fixation device and the loop having an adjustable length/perimeter, the splice of the tensionable construct being pre-built with an additional, fixed loop attached to the spliced loop, the fixed loop having a fixed perimeter; (ii) inserting the first fixation device into bone; (iii) passing the flexible strand around or through tissue to be fixated (or reattached) to bone; (iv) subsequently, attaching the fixed loop to a second fixation device; (v) inserting the second fixation device into bone; and (vi) pulling on the free end to decrease the perimeter of the spliced adjustable loop, to allow the soft tissue to achieve the desired location relative to the bone and to allow proper tensioning of the final construct.

The flexible strand of the knotless tensionable construct may be passed through at least a portion of the body of the first fixation device (for example, through a full cannulation of the first fixation device, or through a transversal opening at a distal end of the first fixation device). Alternatively, the flexible strand may be fixed to the first fixation device (which may be solid or cannulated) by overmolding the suture to the anchor body or by compressing the suture against the bone (achieving an interference fit between the first fixation device and the bone tunnel, compressing the flexible strand). The splice may be formed within the body of the first fixation device or outside the body of the first fixation device. Upon insertion into the bone and tensioning, the splice may reside within the body of the first fixation device or outside the body of the first fixation device.

The fixed (additional) loop may be integral to the flexible strand or may be attached to the flexible strand, i.e., formed as an extra loop attached to the spliced adjustable loop of the knotless tensionable construct.

In an exemplary embodiment only, the first fixation device is a first suture anchor (for example, a 5.5 mm Arthrex Corkscrew® anchor, disclosed in U.S. Pat. No. 6,117,162) modified to carry a suture that is spliced in a manner similar to an Arthrex ACL TightRope®, such as disclosed in U.S. Patent Application Publication Nos. 2010/0256677 and 2010/0268273, the disclosures of which are incorporated by reference herein. The tensionable suture is free with a fixed end (that may be looped or knotted, for example). Once the first suture anchor (the modified 5.5 mm Corkscrew® anchor) has been implanted, the driver is removed and the suture bundle is exposed. The suture bundle is then passed through the tissue (the rotator cuff). The fixed end of the suture is secured to a second fixation device by placing the fixed end through the eyelet of a second anchor (for example, an Arthrex SwiveLock® anchor, disclosed in U.S. Patent Application Publication No. 2008/0004659, or another anchor).

The suture may be looped so that the loop is placed a certain distance away from the splice and is attached to an open ended eyelet of the second anchor (the SwiveLock® anchor). In additional embodiments, the suture is looped and an additional loop (a fixed loop) is attached to the spliced adjustable loop (the splice being pre-built with the extra loop). Alternatively, the suture may be knotted so that the knot is placed a certain distance away from the splice and the knot rests within the opening of the eyelet of the second anchor (the SwiveLock® anchor). In yet another embodiment, the suture may have no modification (i.e., provided with neither a loop nor a knot), in which case the splice will be positioned so that the splice remains just above the anchor/bone level.

Once the second anchor (the SwiveLock® anchor) is implanted, the sutures are tightened by pulling the free ends for tensioning. The ends are then clipped and the steps may be repeated for a second (or multiple) row repair.

Figure 2:
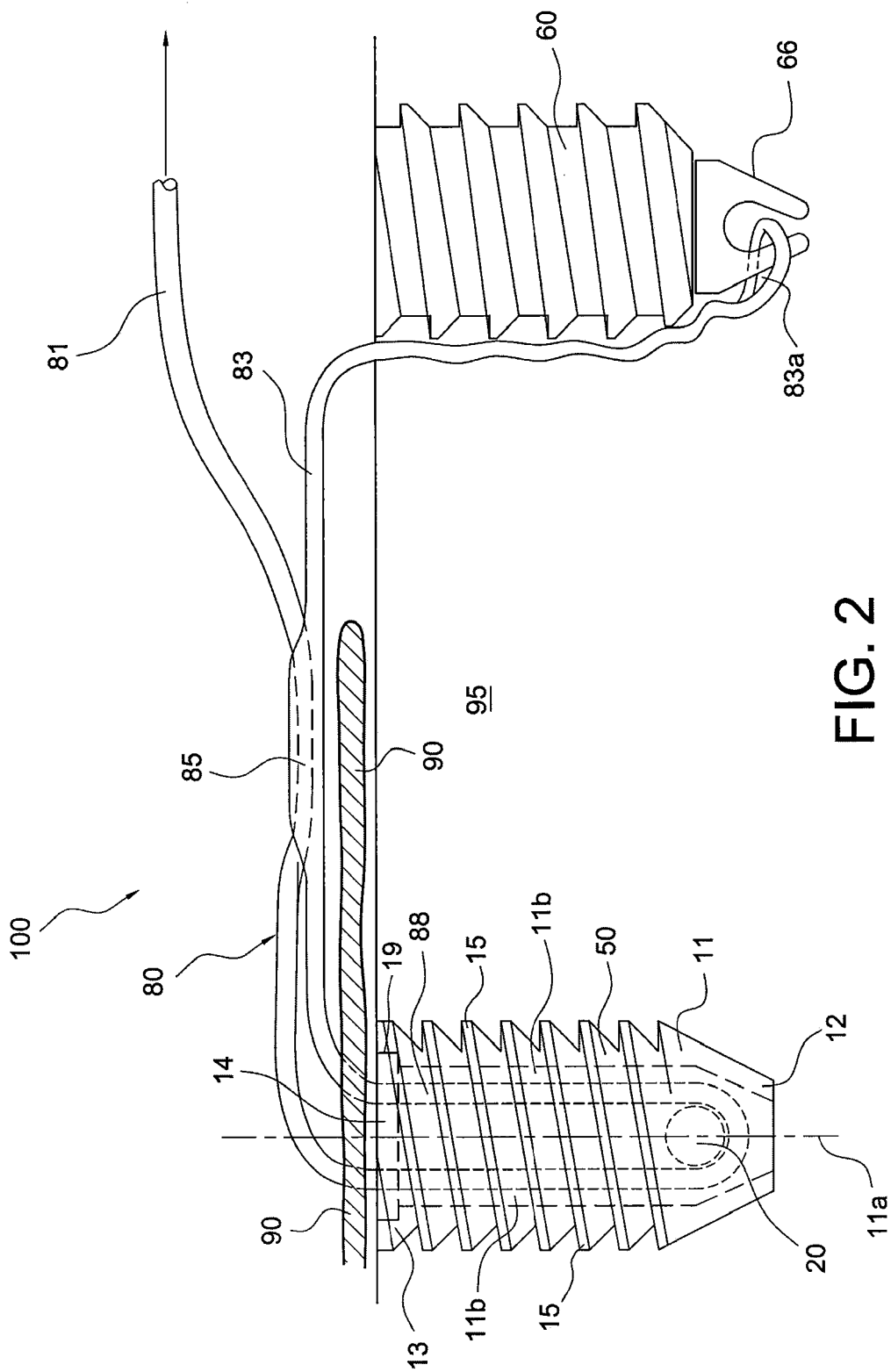
Figure 3:
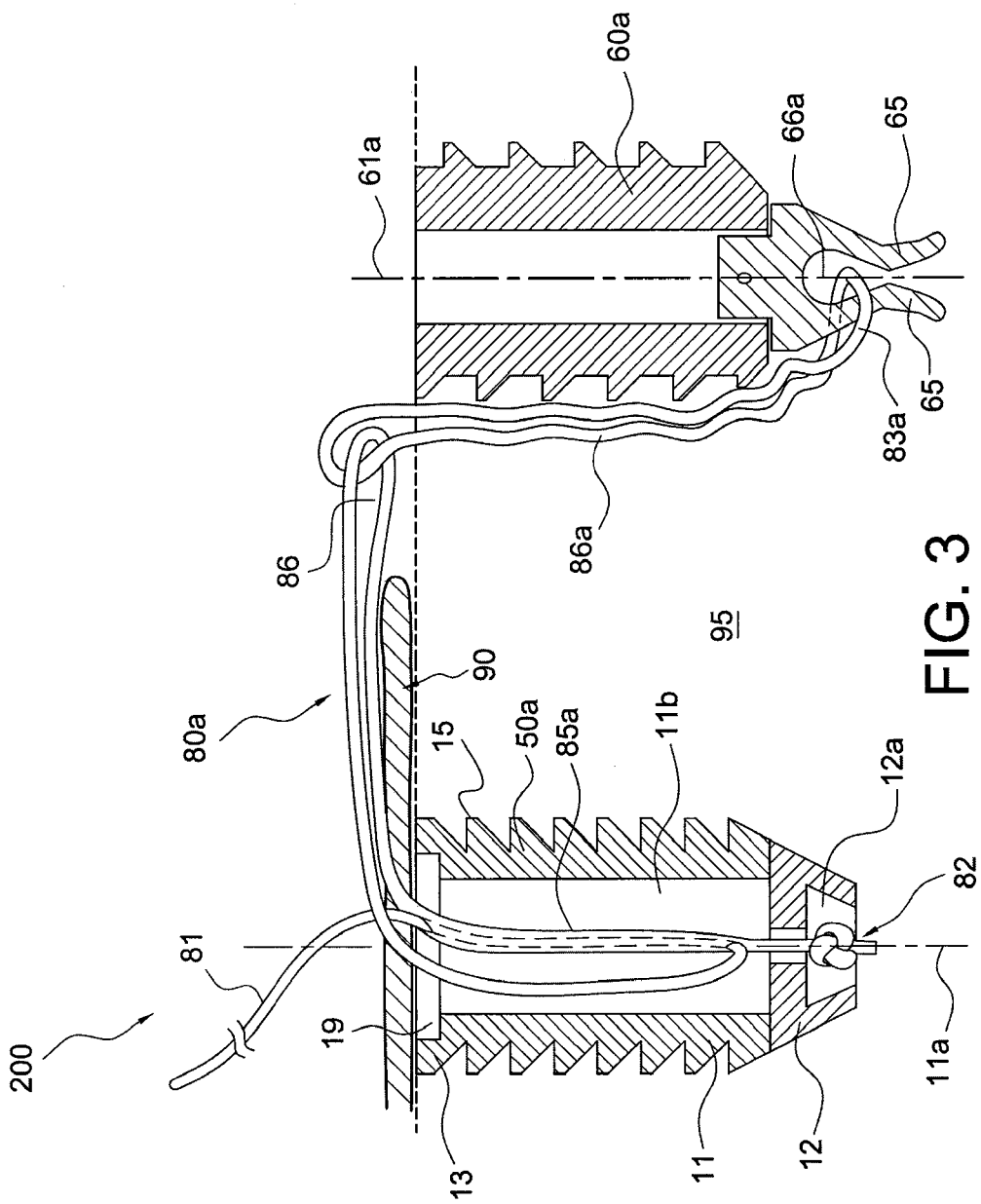
FIG. 3 illustrates a schematic view of an adjustable, tensionable anchor system according to another exemplary embodiment of the present invention.
Figure 4:
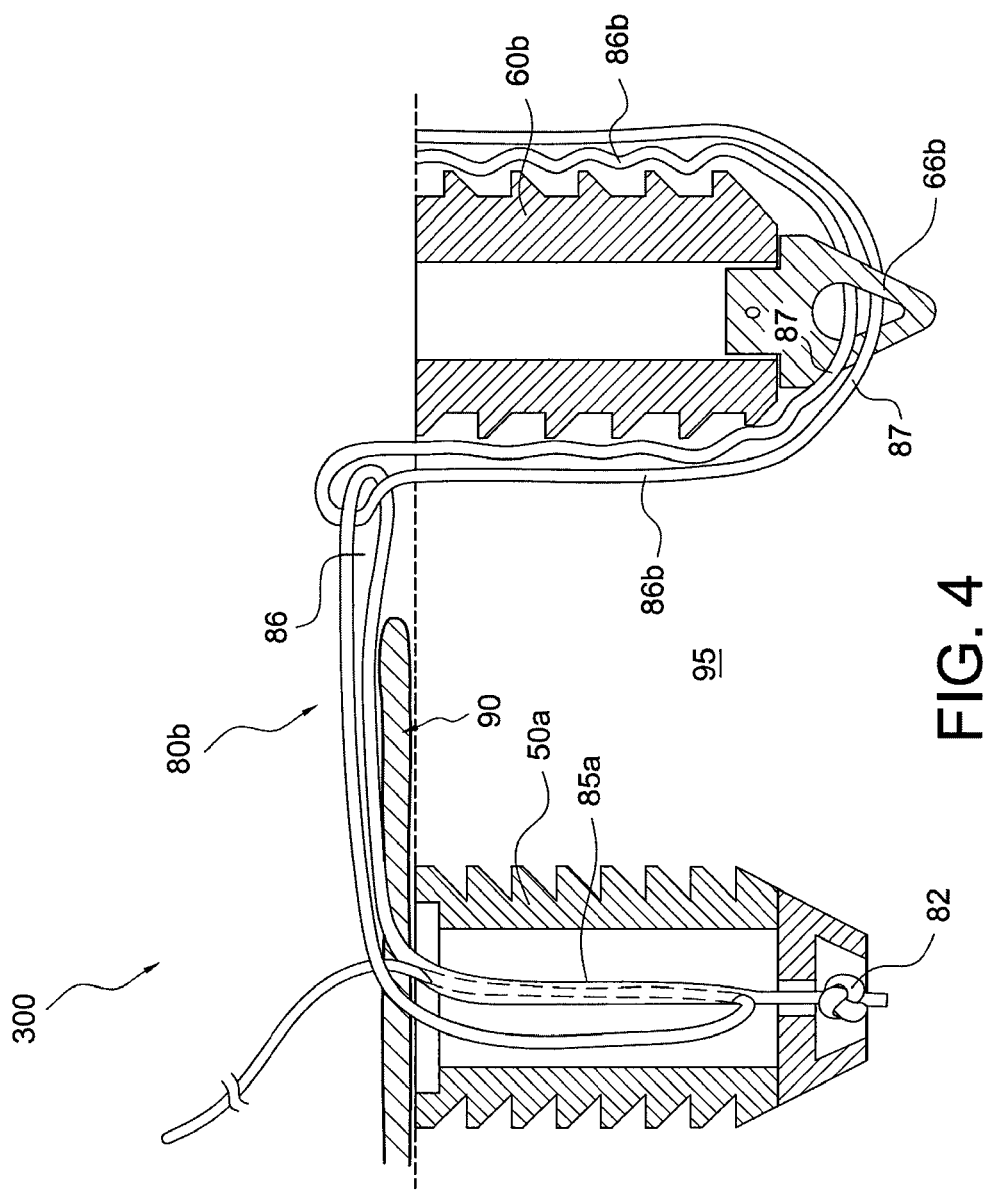
FIG. 4 illustrates a schematic view of an adjustable, tensionable anchor system according to another exemplary embodiment of the present invention.
Figure 5:
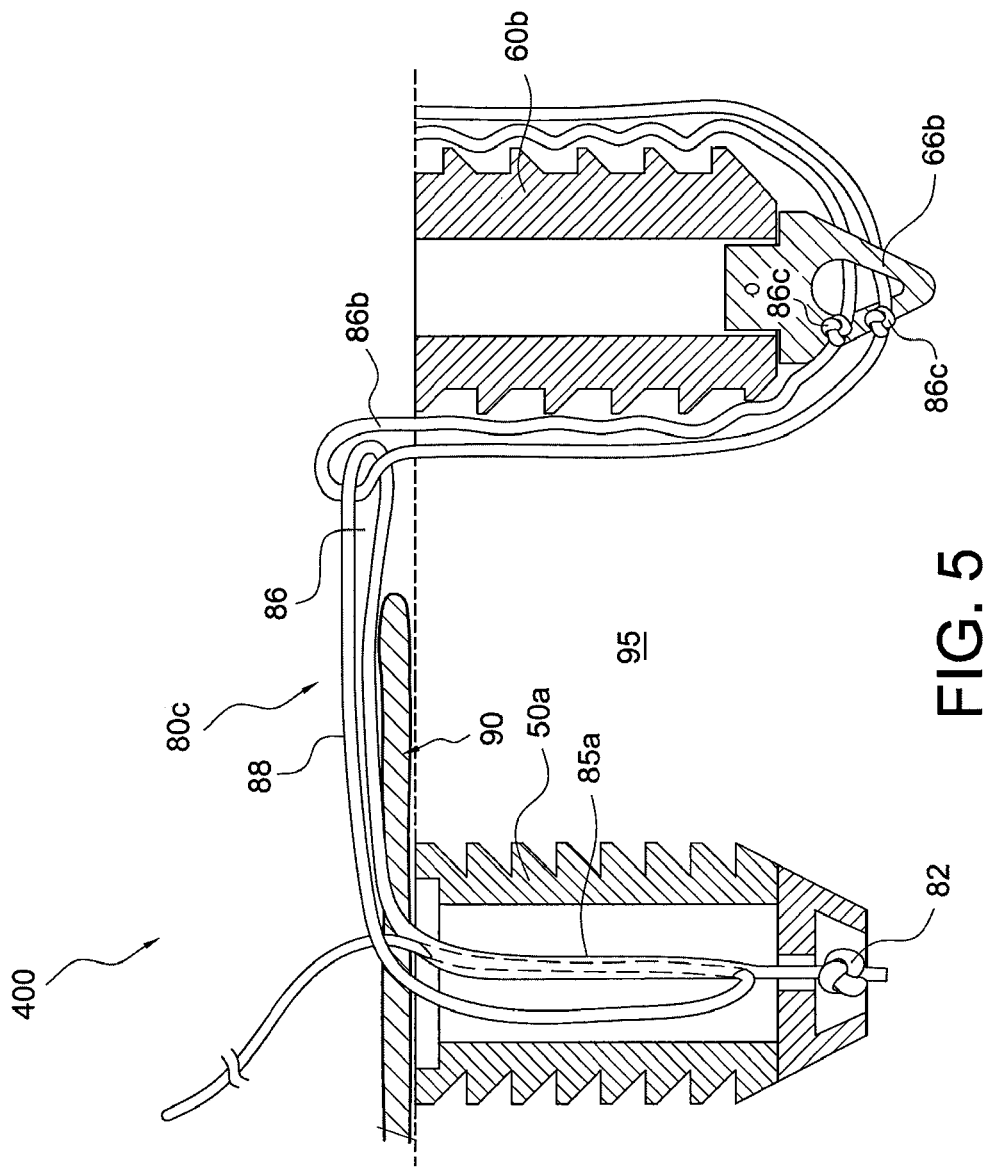
FIG. 5 illustrates a schematic view of an adjustable, tensionable anchor system according to another exemplary embodiment of the present invention.

Referring now to the drawings, where like elements are designated by like reference numerals, FIGS. 1-5 illustrate exemplary tensionable knotless anchor systems 100, 200, 300, 400 of the present invention provided with first and second fixation devices 50, 50a, 60, 60a, 60b and a self-locking, adjustable, tensionable construct 80, 80a, 80b, 80c for knotless tensioning of soft tissue 90. FIGS. 1 and 2 illustrate exemplary anchor system 100 (of a first-type construct). FIGS. 3-5 illustrate exemplary anchor systems 200, 300, 400 (of a second-type construct). FIGS. 6-39 illustrate exemplary steps of a method of soft tissue repair with the exemplary adjustable, knotless, tensionable system 200 of FIG. 3.

FIGS. 1 and 2 illustrate tensionable knotless anchor system 100 (a first-type construct) of the present invention that is provided with a first fixation device 50 (a first knotless anchor 50), a second fixation device 60 (a second knotless anchor 60), and a self-locking, tensionable, adjustable construct 80 (suture mechanism 80) for knotless tensioning of soft tissue 90 (rotator cuff 90). As detailed below, the self-locking, tensionable, adjustable construct 80 extends between the two fixation devices 50, 60 and is attached to each of them.

In the exemplary embodiment illustrated in FIGS. 1 and 2, fixation device 50 is a tensionable knotless anchor having an anchor body 11 provided with a longitudinal axis 11a, a proximal end 13 and a distal end 12, and a plurality of ribs 15 extending circumferentially around it. Cannulation 11b extends along the body 11 and allows threading suture(s) to pass around post 20, i.e., allows passage of a flexible strand 88, as detailed below. Cylindrical portion 14 is provided at the proximal end 13 of the anchor 50 and contains a socket 19 (FIG. 2) configured to securely engage a tip of a driver.

In lieu of the open cannulation, the anchor body may include a pair of openings/channels that are positioned opposite to each other relative to the post 20 and also symmetrically located relative to (and parallel with) longitudinal axis 11a, to allow flexible strand or flexible material 88 (suture 88) to pass and slide therethrough.

Anchor 50 may be a screw-in anchor or a push-in style anchor. Anchor 50 may be formed of metal, biocompatible plastic such as PEEK or a bioabsorbable PLLA material. Socket 19 at the distal end 13 of the anchor 50 is configured to securely engage a tip of a driver. The socket of the anchor 50 may have any shape adapted to receive a driver tip for pushing tap-in or screw-in style anchors. Tensionable knotless anchor 50 may be made of one or more pieces, or may be provided as an integrated device.

In an exemplary and illustrative-only embodiment, the first knotless anchor 50 is a modified 5.5 mm Corkscrew® anchor 50 and the second knotless anchor 60 is a SwiveLock® anchor 60 with an open distal eyelet 66 (as disclosed and described in U.S. Patent Application Publication No. 2007/0191849, the disclosure of which is hereby incorporated by reference in its entirety).

Adjustable, tensionable, self-locking construct 80 is a suture assembly 80 which may be formed by splicing flexible strand or flexible material 88 (for example, suture 88) through itself to form a splice 85, a spliced adjustable loop 86 (having an adjustable length/perimeter), a free end 81 (a pull cord 81) and a fixed end 83. Self-locking construct 80 extends between, and is attached to, the two knotless anchors 50, 60 (as shown in FIGS. 1 and 2) and ensures fixation of rotator cuff 90 against the bone, with tensioning of the rotator cuff 90 after implantation of anchors 50, 60. In the exemplary embodiment shown in FIGS. 1 and 2, the free end 83 is in the form of a fixed loop 83a formed in the free end (as part of the free end of the suture 88) having a fixed perimeter. However, the free end 83 may be also in the form of a knot or of any other structure that allows secure attachment to second fixation device 60 (as detailed below). The fixed loop 83a is removably attached to the distal eyelet 66.

Once the modified 5.5 mm Corkscrew® anchor has been implanted, the driver is removed and the suture bundle of the suture assembly 80 is exposed. The suture bundle is then passed through the rotator cuff 90. The fixed loop 83a is then attached to the second fixation device 60, i.e., the fixed loop 83a is placed through the eyelet 66 of the SwiveLock® anchor 60. In one embodiment and as illustrated in FIGS. 1 and 2, the fixed suture end 83 may be looped so that loop 83a is positioned a certain distance away from the splice 85 and is captured in the open ended eyelet 66 of the SwiveLock® anchor 60. Alternatively, the fixed end 83 may be knotted so that the knot is a certain distance away from the splice 85 and the knot is captured in the opening of the eyelet 66 of the SwiveLock® anchor 60. The fixed end 83 may also have no modification (i.e., no loop or knot), in which case the splice 85 will be positioned so that the splice remains just above the anchor/bone level. In this embodiment, the fixed end will be just a free end of the suture 88 that is inserted into a closed eyelet of another fixation device (for example, a closed eyelet of a SwiveLock® anchor).

An exemplary method of rotator cuff repair with the adjustable, knotless, tensionable system 100 of FIGS. 1 and 2 begins, for example, by preparing a punch hole within bone 95 underneath the rotator cuff tissue 90, for use in the medial row. A modified Corkscrew® anchor 50 (for example, a modified 5.5 mm Corkscrew® anchor 50) with suture loop 86 of the suture assembly 80 is inserted into a punched hole with a driver. The driver is removed and the suture assembly 80 is left hanging out from the end of the modified Corkscrew® anchor 50. The suture assembly 80 is pulled through the tissue 90 and all the slack is pulled. The suture assembly 80 contains a splice 85, followed by a free end 81 (pull cord 81) and a suture loop 83a of a fixed perimeter. A punch may be used to prepare a punch hole for SwiveLock® anchor 60 (having open eyelet 66) in the lateral row. A cannulated fixation device (which may be a screw, such as a cannulated interference screw) is inserted over the cannulated shaft of the driver and, during use, is advanced and fully seated on the driver tip and eyelet 66. Suture loop 83*a* of the suture assembly 80 is loaded onto the eyelet 66 of the SwiveLock® anchor 60 and the suture is pulled taut. The SwiveLock® anchor 60 loaded with the suture is inserted into the punch hole. The splice 85 is preferably above the path of the threads, so as to not get pinched. The SwiveLock® anchor 60 is inserted completely. Pull cord 81 of the suture assembly 80 is grasped and pulled. Slack gets shuttled and pulled through the modified Corkscrew® anchor 50. Suture splice 85 holds rotator cuff tissue 90 against bone 95. The steps may be repeated as desired, for additional anchor fixation and multiple rows formation.

An exemplary method of attaching tissue to bone with the construct 100 of FIGS. 1 and 2 comprises inter alia the steps of: (i) providing surgical construct 100 comprising a fixation device 50 (for example, an anchor) with an adjustable, tensionable construct 80 attached to (pre-loaded onto) the fixation device 50, the knotless tensionable construct 80 consisting of a flexible strand 88 with a splice 85, a spliced adjustable loop 85*b*, a free end 81 and a fixed loop 83*a*; (ii) inserting the fixation device 50 with the attached (pre-loaded) knotless tensionable construct at a first location into bone 95; (iii) securing the fixed loop 83*a* of the flexible strand 88 at a second location into bone 95 with another fixation device 60; and (iv) pulling on the free end 81 to tension the final construct.

FIGS. 3-5 illustrate embodiments (surgical constructs 200, 300, 400) of a second-type construct of the present invention. The second-type constructs (tensionable knotless anchor constructs 200, 300, 400) are similar in part to the tensionable knotless anchor system 100 in that they are also provided with first and second fixation devices 50*a*, 60*a*, 60*b*, 60*c* and a self-locking, adjustable, tensionable construct 80*a*, 80*b*, 80*c* for knotless tensioning of soft tissue 90. These second-type constructs differ, however, from the first-type construct mainly in the location of the fixed point (fixed end). Specifically, the second-type constructs include a knotted end (fixed end) that is placed on the first fixation device, which allows the splice to be contained in the body of the first fixation device. Thus, the first fixation device (anchor construct) is modified so that splice 85*a* is located within the anchor body, and the size of the fixed loop attached to the second anchor has been increased. These modifications help the surgeon to eliminate guessing as to where the splice will end up when the final construct is all tensioned. It also moves the tension point for easier tensioning. It also allows for the anchors to be located closer together (i.e., to be located at a distance less than the length of the splice). The eyelet of the second fixation device 60*a* is also modified to a design wherein the open distal eyelet has a convex configuration (with arms flaring out of the body of the fixation device) that allows the loop to slide between the arms but is more difficult to remove the loop due to the curvature of the arms of the eyelet. The splice is also provided with an already pre-built extra suture loop attached.

As detailed below, the second-type surgical constructs 200, 300, 400 comprise a fixation device (a suture anchor) with an attached (pre-loaded) tensionable construct formed of a flexible strand with a free end, a spliced adjustable loop (located within the body of the fixation device), and a knotted fixed end or insert molded fixed end. An attachment device or mechanism in the form of a fixed loop (a second loop) is attached to the spliced adjustable loop for further attachment to another fixation device (a second fixation device). The knotted end (fixed end) is located on the fixation device (suture anchor), allowing the splice to be contained within the anchor body and allowing the two fixation devices to be placed closer together. With this exemplary type of construct, the second fixation device may be any type of fixation device, for example, swivel and/or screw-in suture anchors and/or push-in suture anchors, or even staples or similar devices. The attachment device (the second loop or fixed loop) in this construct is acting like a pulley or pivot point when it is attached to the second fixation device. The attachment device may be also an additional separate free strand that is passed through the adjustable loop and then captured by the closed eyelet of the SwiveLock® anchor, or a free strand with at least one knot that is captured with a closed eyelet of the SwiveLock® anchor, or similar arrangements.

Other embodiments of this second-type construct include: (i) replacing the second loop with a separate free suture used with a closed eyelet SwiveLock® anchor, so that the free suture is passed through the adjustable loop and then captured by the closed eyelet of the SwiveLock® anchor and positioned to keep the adjustable loop above the second anchor; or (ii) replacing the second loop with a free suture with one or more knots (for example, two knots located at a set distance apart from each other), passing the free suture through the adjustable loop and capturing the knots with a closed eyelet of the SwiveLock® anchor; or (iii) eliminating the second loop altogether and capturing the spliced adjustable loop with another fixation device (such as a staple, for example, or a modified SwiveLock® anchor that allows passing of the adjustable loop through a cannulation of the anchor body).

Surgical construct 200 is shown in FIG. 3. Surgical construct 200 comprises a fixation device 50*a* (a suture anchor 50*a*) with an attached (pre-loaded) tensionable construct 80*a* formed of a flexible strand 88 with a free end 81, a splice 85*a* (located within the body of the fixation device) with a spliced adjustable loop 86, and a knotted fixed end 82 or insert molded fixed end. Attachment device 86*a* (fixed loop 86*a* or second loop 86*a*) is attached to the spliced adjustable loop 86 for further attachment to another fixation device 60*a* (a second fixation device 60*a*).

Fixation device 50*a* is a tensionable knotless anchor having an anchor body 11 provided with a longitudinal axis 11*a*, a proximal end 13 and a distal end 12, and a plurality of ribs 15 extending circumferentially around it. Cannulation 11*b* extends along the whole length of body 11 to allow passage of a flexible strand 88 and splice 85*a* and to secure knot 82. Proximal end 13 of the anchor 50*a* contains a socket 19 (FIG. 3) configured to securely engage a tip of a driver.

Anchor 50*a* may be a screw-in anchor or a push-in style anchor. Anchor 50*a* may be formed of metal, biocompatible plastic such as PEEK or a bioabsorbable PLLA material. Socket 19 at the distal end 13 of the anchor 50*a* is configured to securely engage a tip of a driver, as detailed below. The socket of the anchor 50*a* may have any shape adapted to receive a driver tip for pushing tap-in or screw-in style anchors. Tensionable knotless anchor 50*a* may be made of one or more pieces, or may be provided as an integrated device.

Tensionable knotless anchor 50*a* is preferably provided pre-loaded (pre-assembled) with the construct 80*a*. Anchor 50*a* may be assembled with construct 80*a* by employing a shuttle/pull device (a suture passing instrument such as FiberLink™ or a nitinol loop) attached to the flexible strand (as detailed in U.S. application Ser. No. 13/615,986, filed Sep. 14, 2012, the disclosure of which is incorporated in its entirety herewith). Static knot 82 (fixed end 82) prevents suture 88 from passing through distal blind hole 12a. The suture may also be preloaded by insert molding or by any other means known in the art.

Tensionable knotless construct 80a also includes a suture loop end 86a which may be in the form of a fixed loop 86a (having a fixed length perimeter) securely attached to the adjustable spliced loop 86 (having an adjustable length perimeter). Second fixation device 60a is a modified SwiveLock® anchor 60a (as disclosed in U.S. Patent Application Publication No. 2008/0004659, the disclosure of which is incorporated in its entirety herewith) but with arms 85 of distal eyelet 66a modified, in that the arms extends away (flare away) relative to longitudinal axis 61a (shown in FIG. 3), having a convex configuration (i.e., a lyre shape configuration).

FIG. 3 depicts the tensionable knotless anchors 50a, 60a after they have been inserted into drilled holes in bone, at two different locations.

FIG. 4 illustrates surgical construct 300 (of the second-type) which is similar to construct 200 of FIG. 3 but differs in that the attachment device 86a (second (fixed) loop 86a) of construct 200 has been replaced with a separate free suture 86b used with a closed eyelet 66b of SwiveLock® anchor 60b. The free separate suture 86b is passed through the spliced adjustable loop 86 (folded over) and then the two folded strands 87 (folded ends 87) are captured by closed eyelet 66b of the SwiveLock® anchor 60b and tensioned to keep the spliced adjustable loop 86 above the second anchor.

FIG. 5 illustrates surgical construct 400 (of the second-type) which is similar to construct 200 of FIG. 3 but differs in that the attachment device 86a (second (fixed) loop 86a) of construct 200 has been replaced with a separate free suture 86b with one or more knots 86c (for example, two knots 86c located at a set distance apart from each other). The free suture 86b is passed through the adjustable spliced loop 86 (folded over) and the static knots 86c are captured with a closed eyelet 66b of the SwiveLock® anchor 60b.

FIGS. 6-39 illustrate exemplary steps of a method of rotator cuff repair 300 with the adjustable, knotless, tensionable system 200 of FIG. 3, and according to an exemplary embodiment of the present invention.

Figure 6:
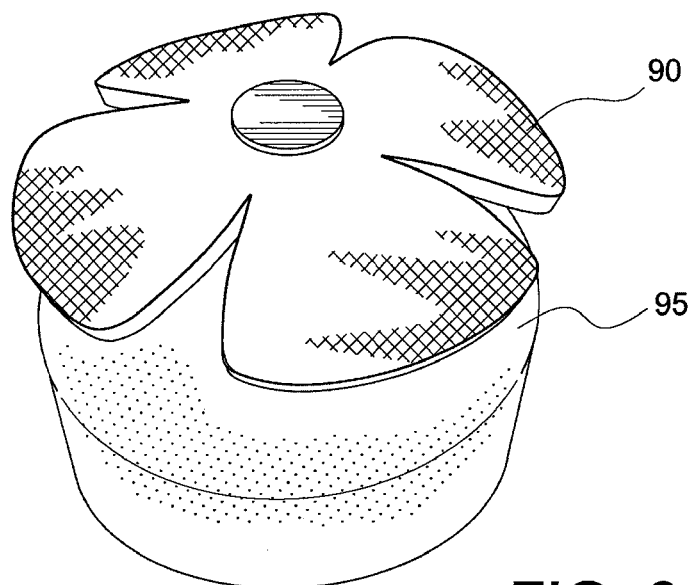
FIGS. 6-39 illustrate exemplary steps of a method of rotator cuff repair with the adjustable, tensionable system of FIG. 3, and according to an exemplary embodiment of the present invention.
Figure 7:
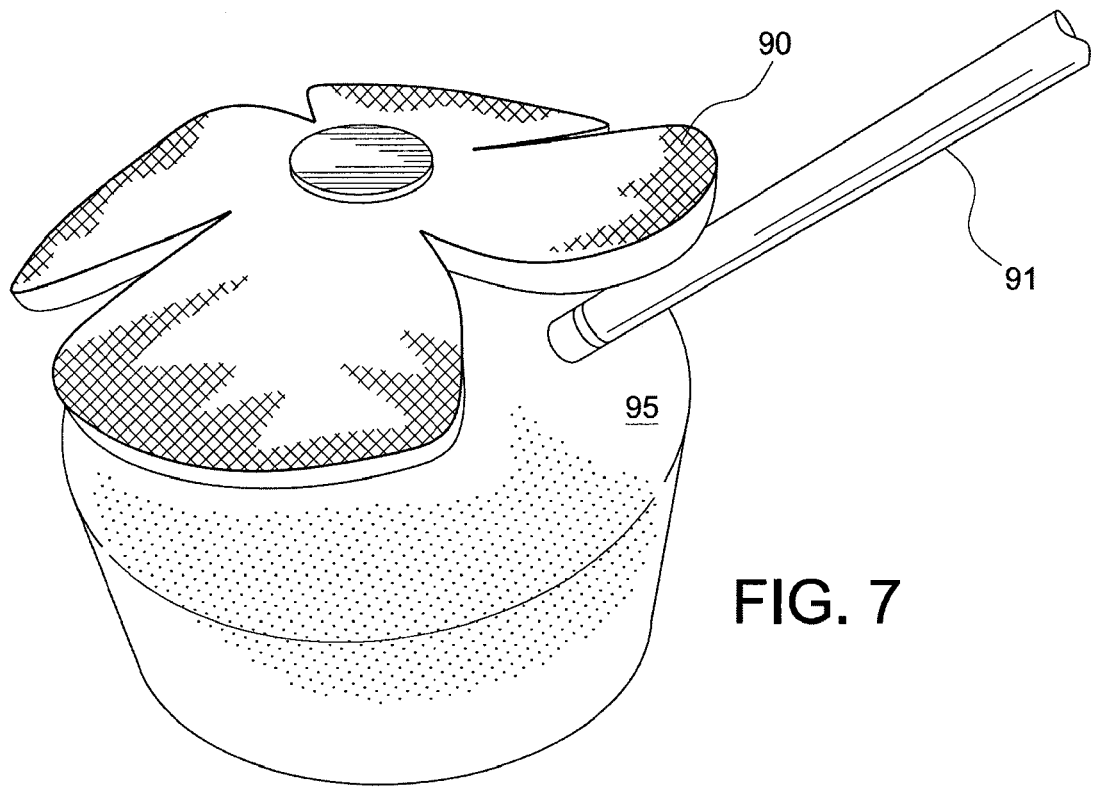

FIGS. 6 and 7: A punch 91 is used to prepare a punch hole 91a within bone 95 underneath the rotator cuff tissue 90, for use in the medial row.

Figure 8:
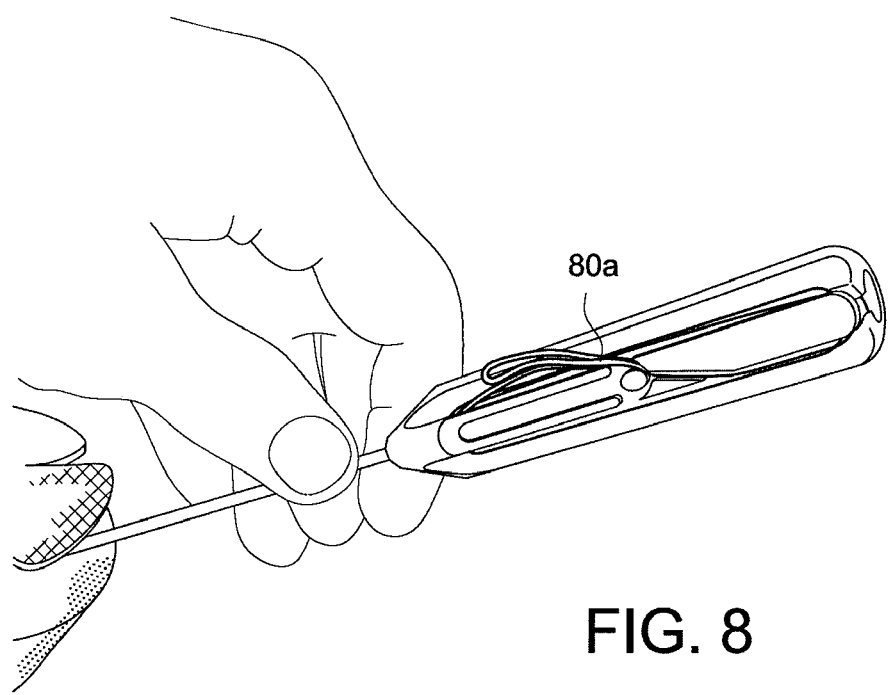
Figure 9:
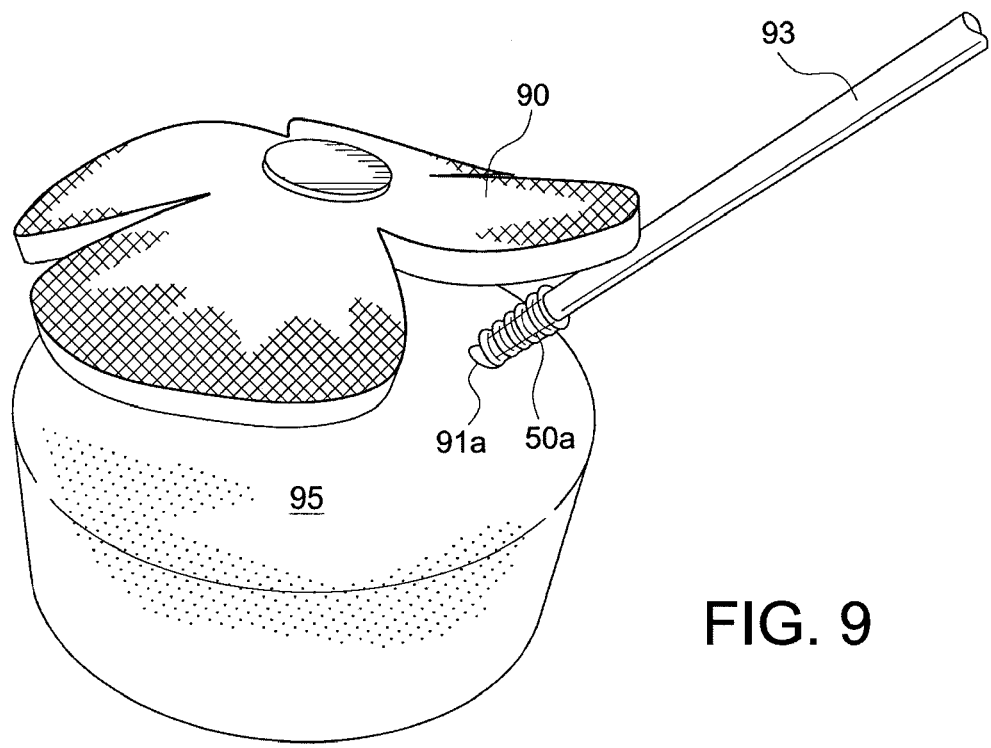

FIGS. 8 and 9: Modified Corkscrew® anchor 50a (for example, a modified 5.5 mm Corkscrew® anchor 50a) with suture loops 86, 86a and splice 85 of the suture assembly 80a is inserted into punched hole 91a with driver 93.

Figure 10:
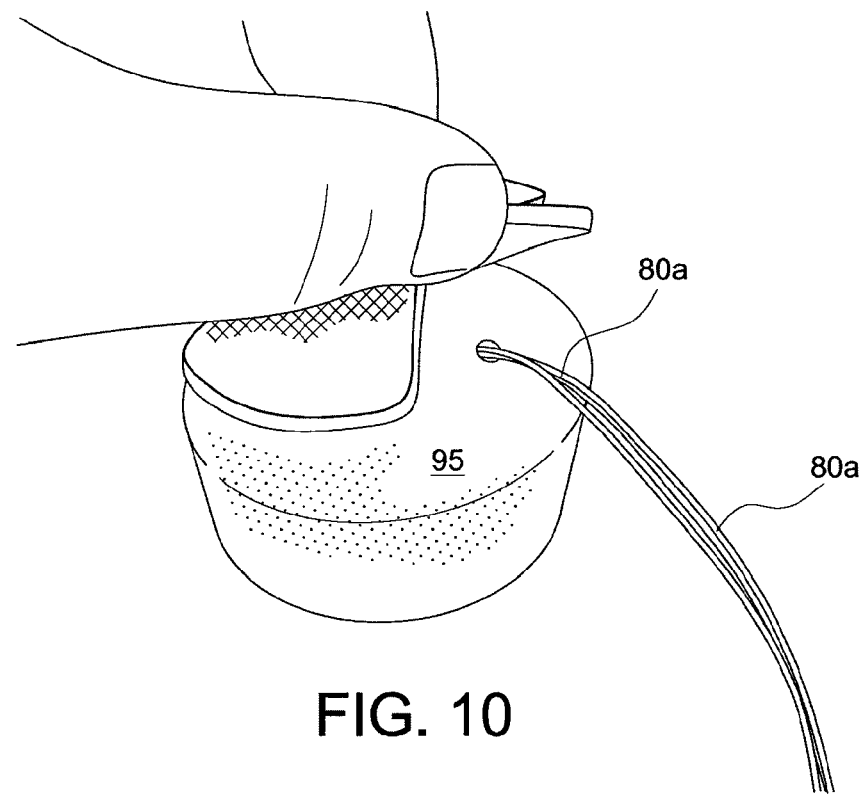
Figure 11:
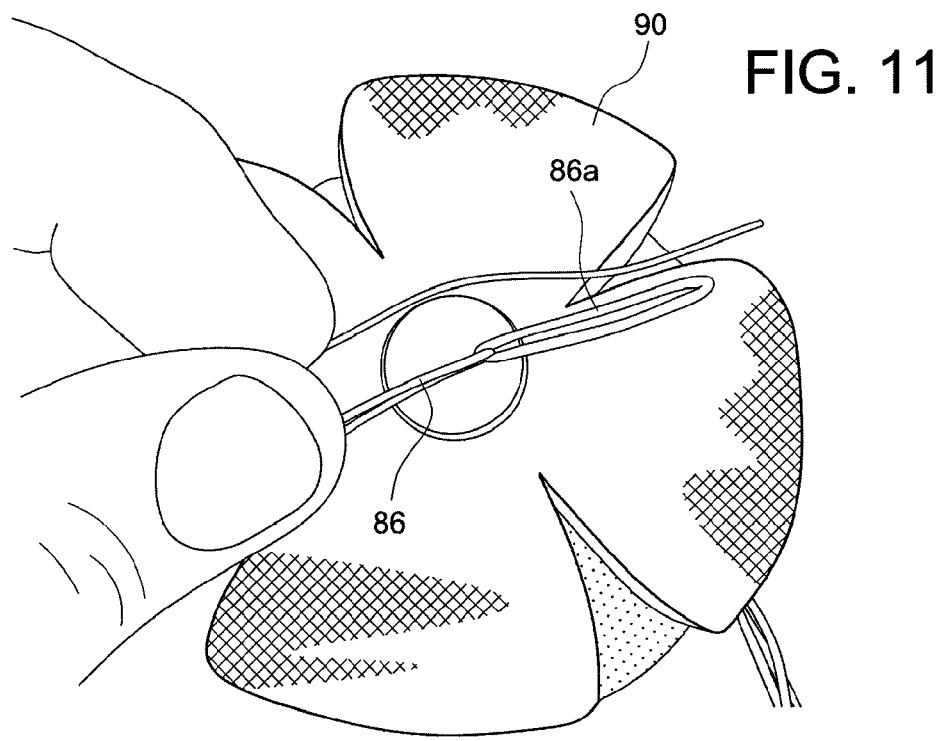

FIGS. 10 and 11: Driver 93 is removed and the suture assembly 80a is left hanging out from the end of the modified Corkscrew® anchor 50a. Interconnected loops 86, 86a are shown in FIG. 11.

Figure 12:
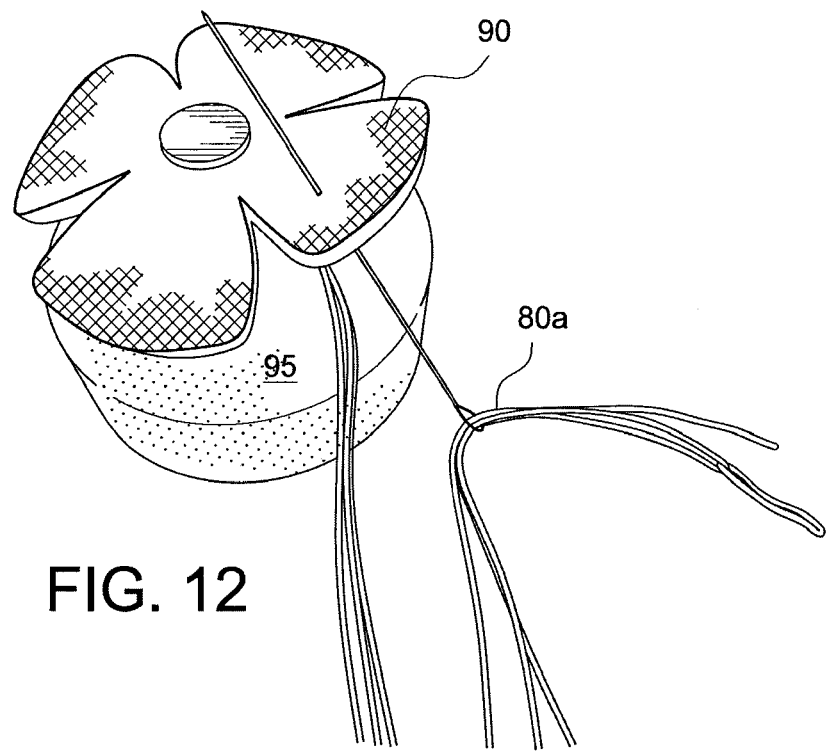
Figure 13:
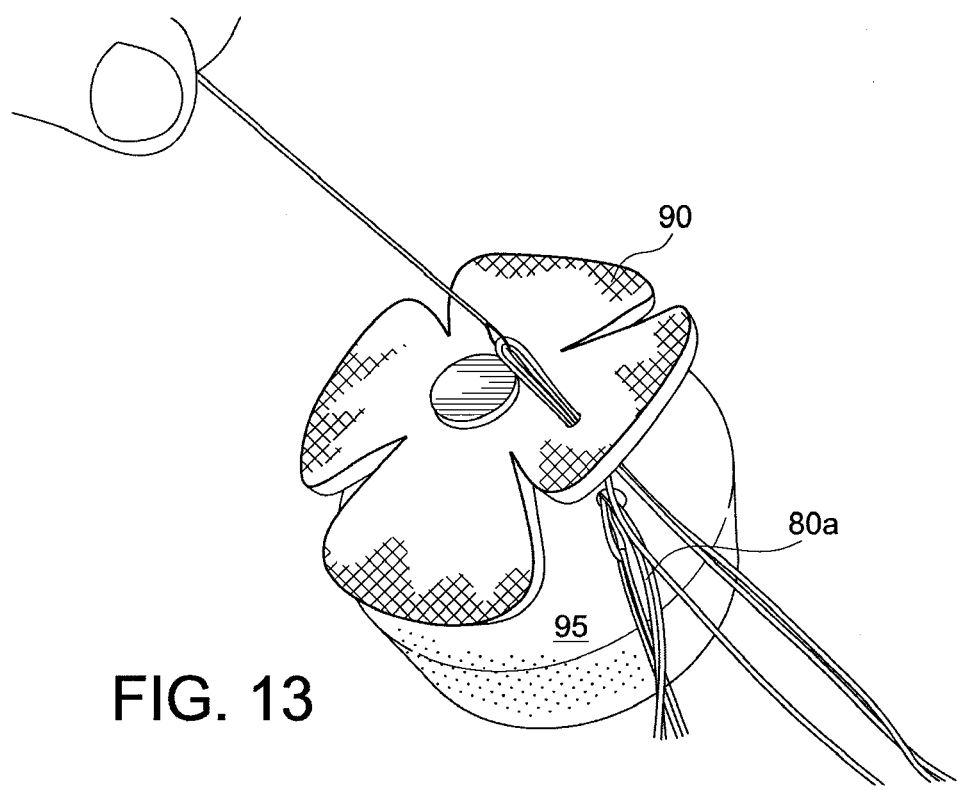
Figure 14:
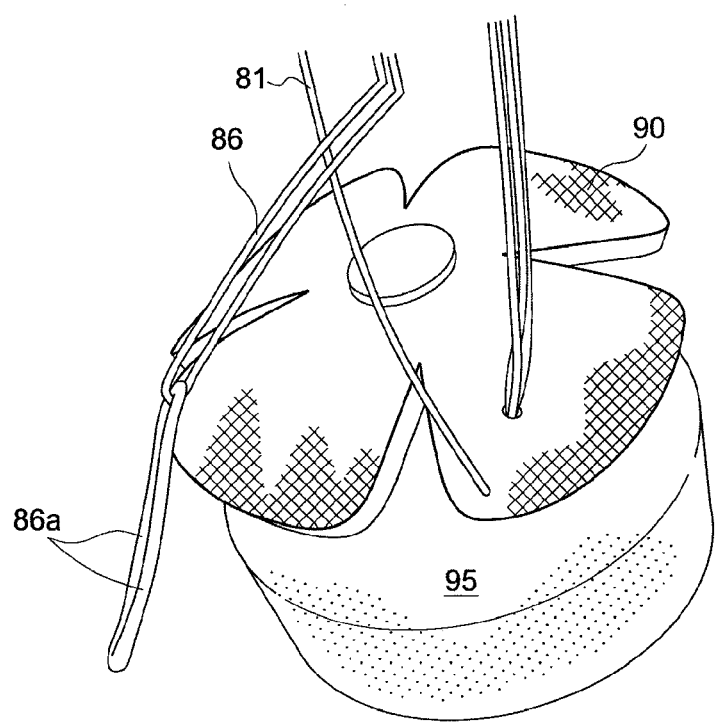

FIGS. 12-14: The suture assembly 80a is pulled through the tissue 90 using a suture passing instrument and all the slack is pulled. The suture assembly 80a contains suture loops 86, 86a, splice 85, followed by a pull cord 81 and a suture loop 83a.

Figure 15:
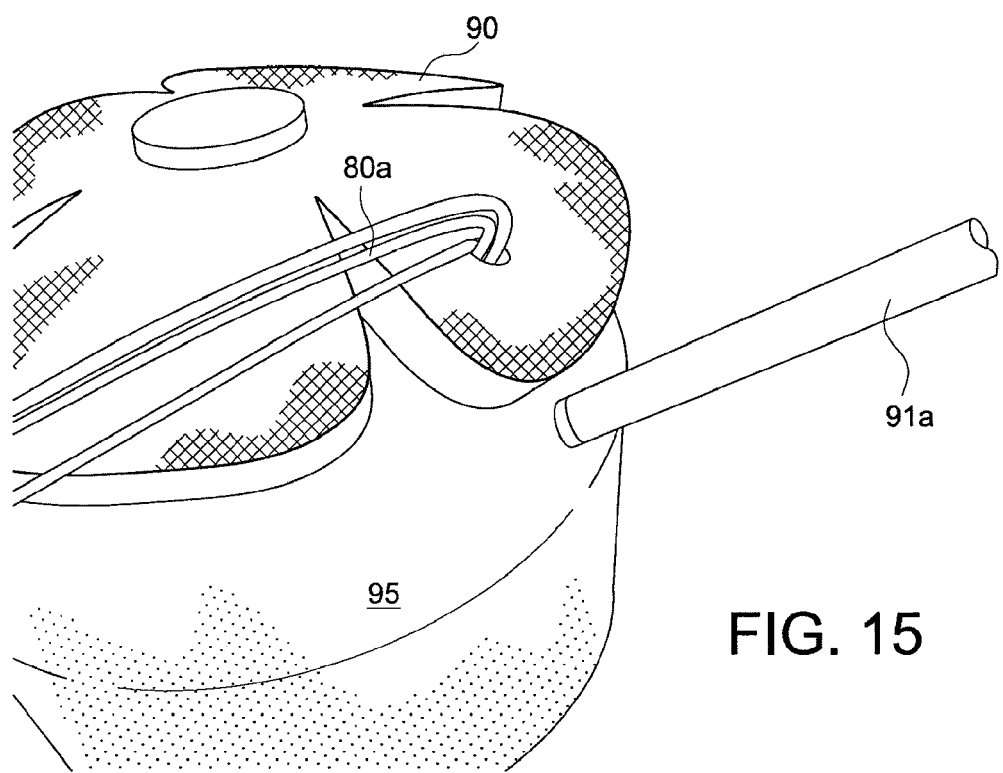

FIG. 15: A punch 91a is used to prepare a punch hole for SwiveLock® anchor 60a in the lateral row.

Figure 16:
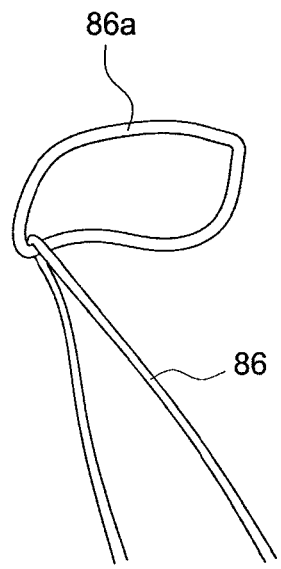
Figure 17:
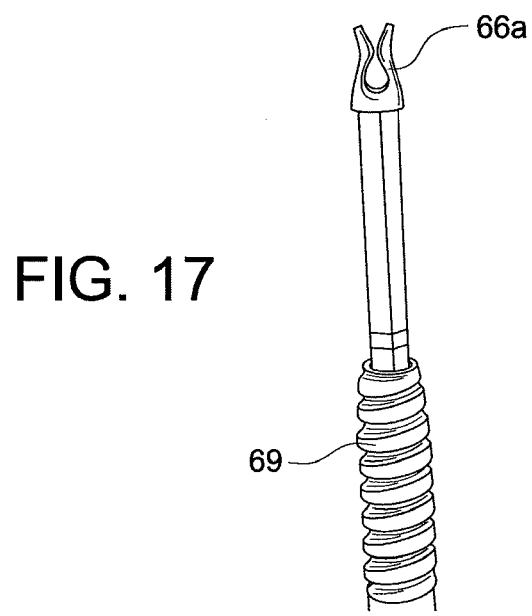
Figure 21:
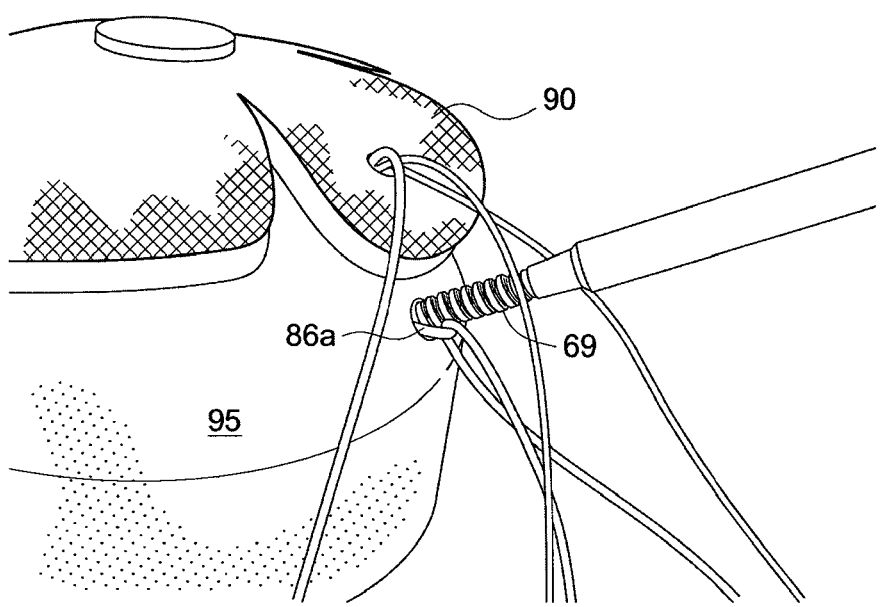
Figure 22:
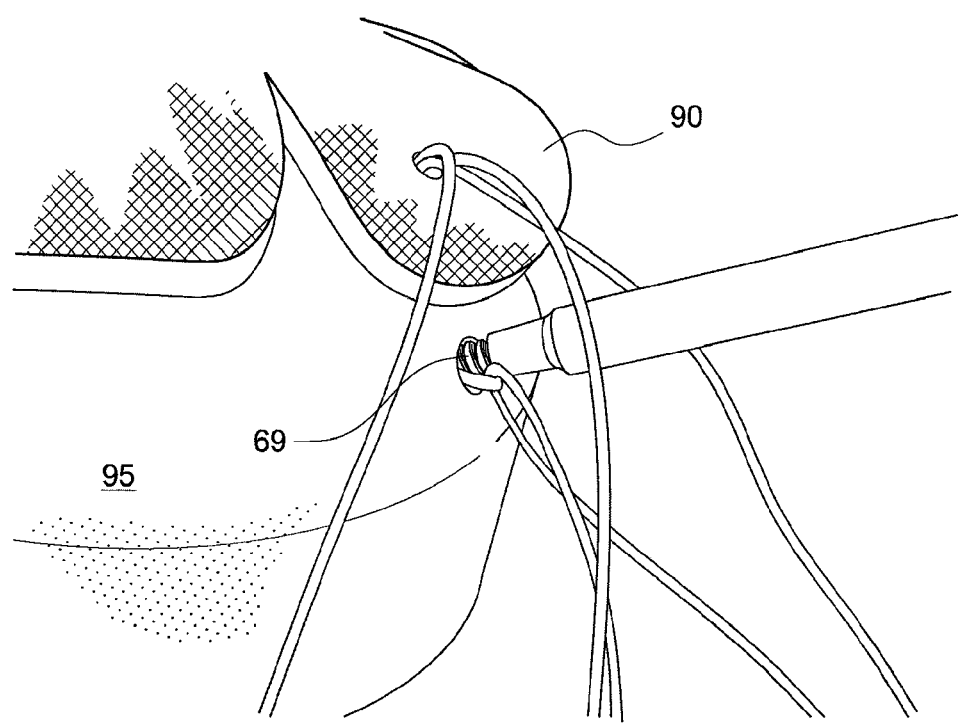
Figure 23:
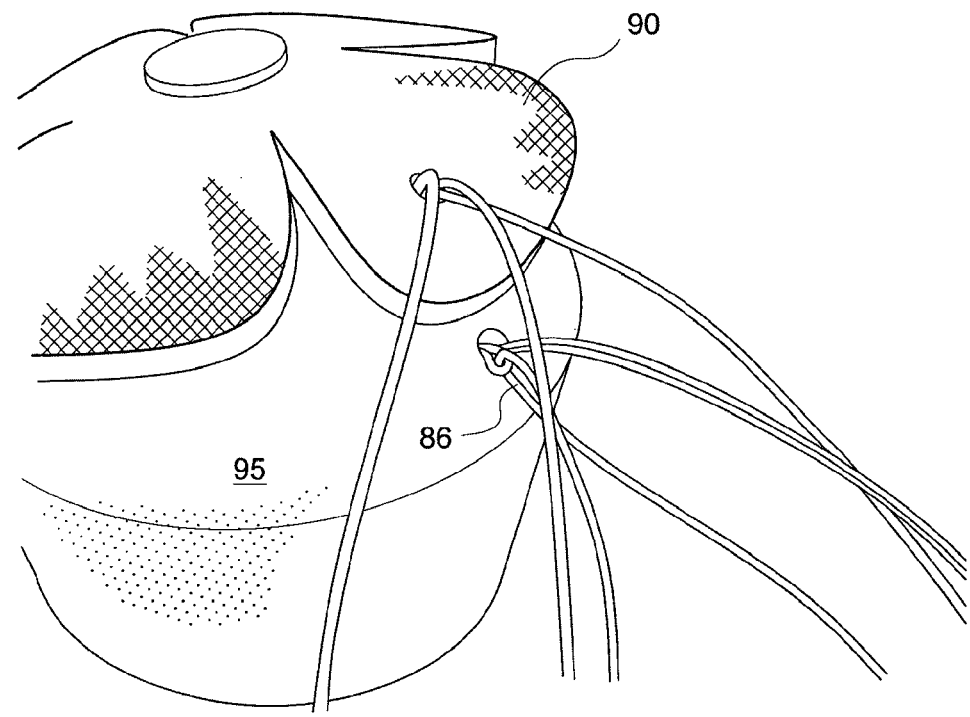

FIGS. 16 and 17: SwiveLock® anchor 60a modified with open eyelet 66a is employed to capture loop 86a having a fixed length/perimeter (FIG. 16). Cannulated fixation device 69 may be a screw, such as a cannulated interference screw, that is inserted over the cannulated shaft 63 of the driver and, during use (and as shown in FIG. 21), is advanced and fully seated on the driver tip and eyelet 66a.

Figure 18:
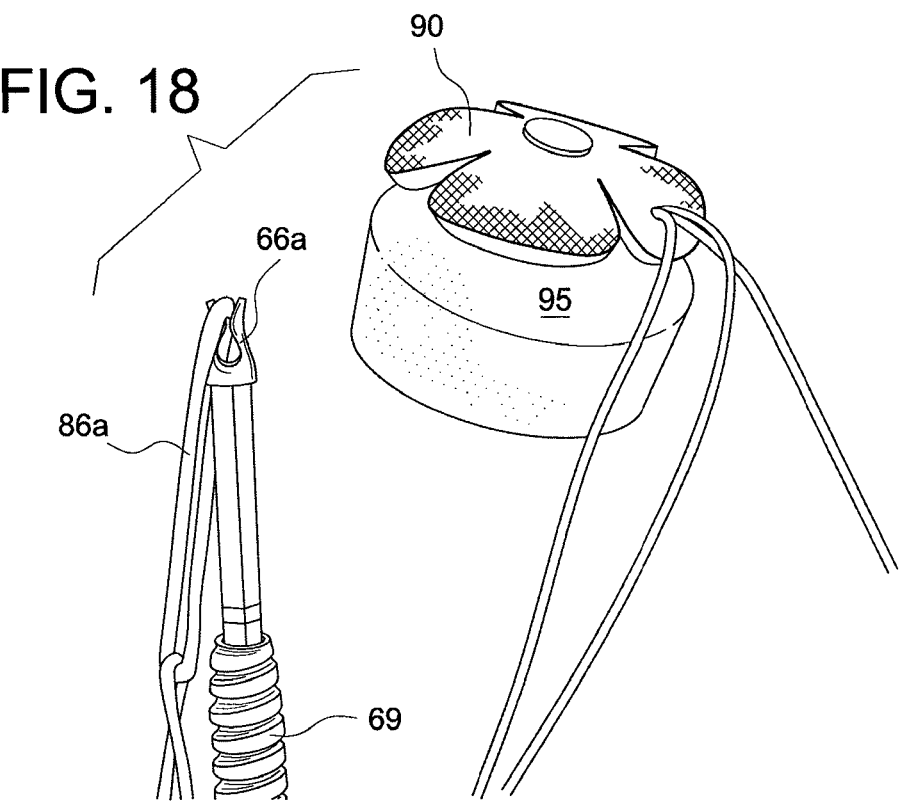
Figure 19:
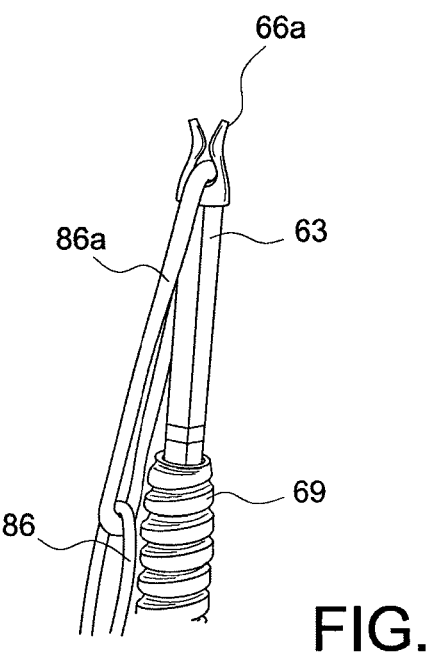
Figure 20:
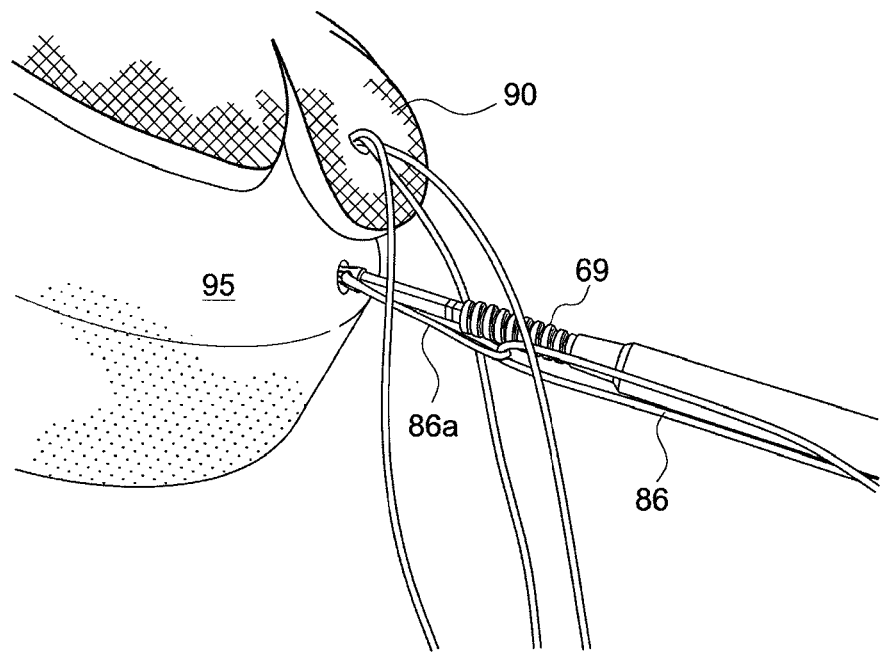

FIGS. 18 and 19: Suture loop 86a of the suture assembly 80a is loaded onto the eyelet 66a of the SwiveLock® anchor 60a and the suture is pulled taut.

FIGS. 20-23: The SwiveLock® anchor 60a loaded with the suture loop 86a is inserted into the punch hole.

Figure 24:
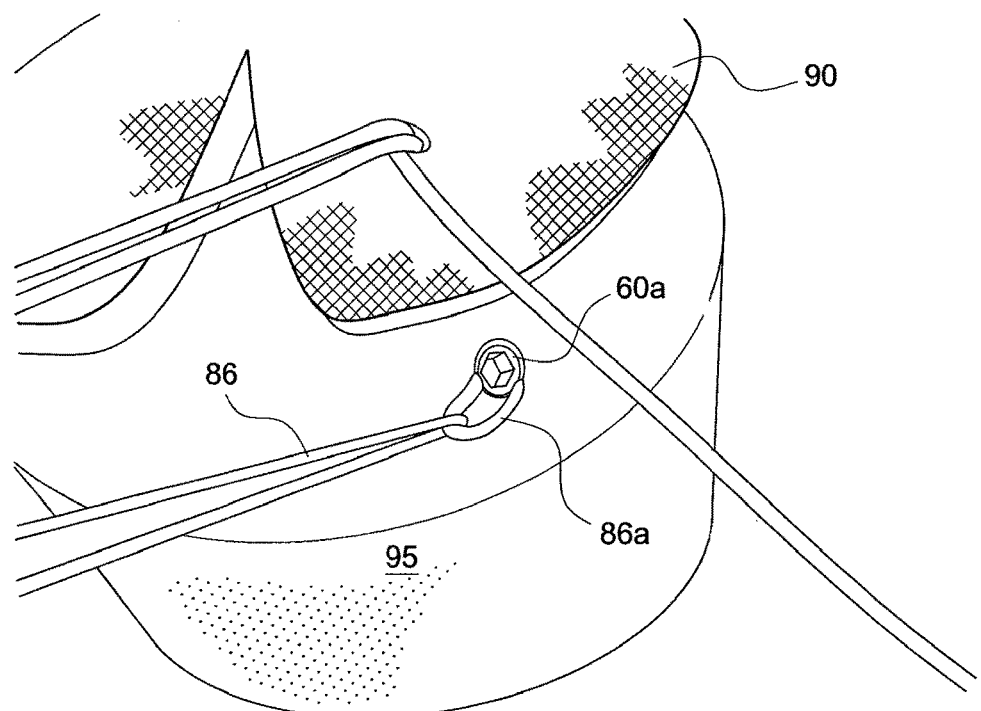

FIG. 24: The SwiveLock® anchor 60a is inserted completely.

Figure 25:
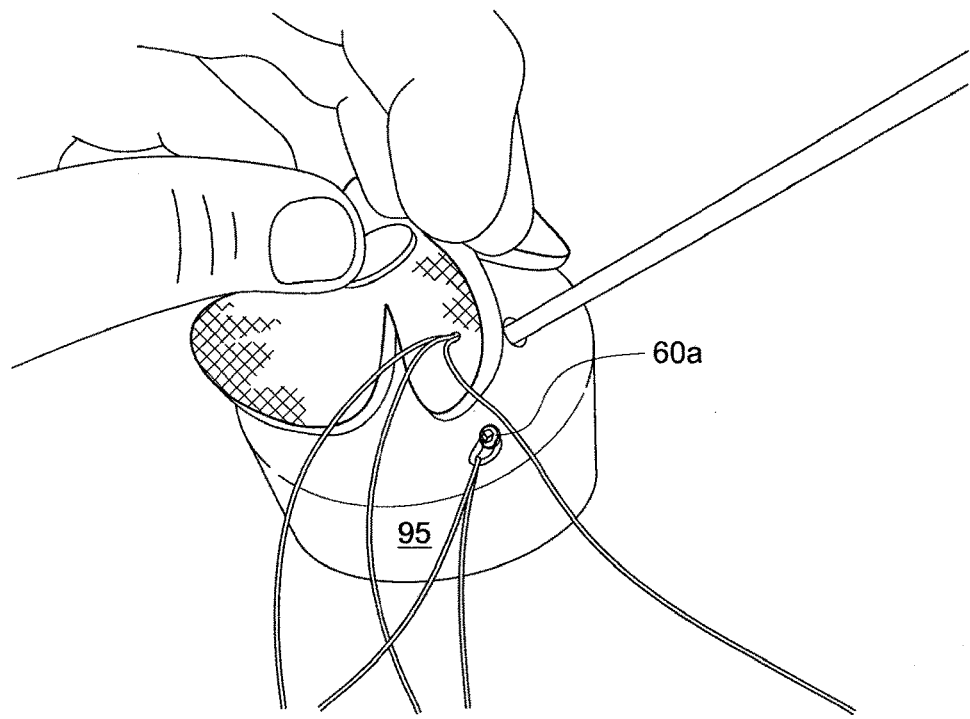
Figure 26:
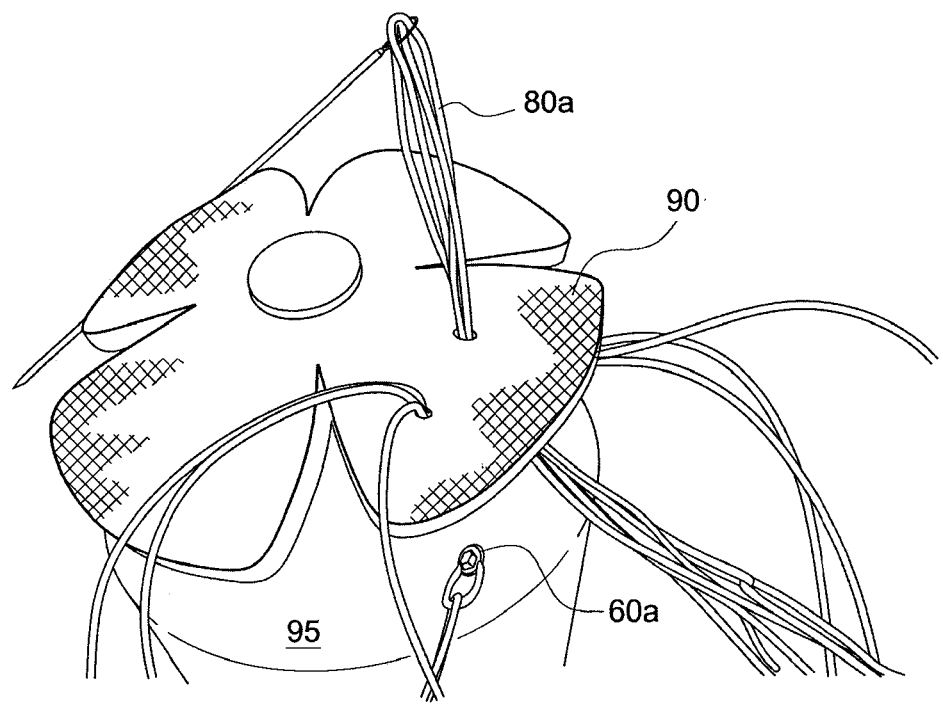
Figure 27:
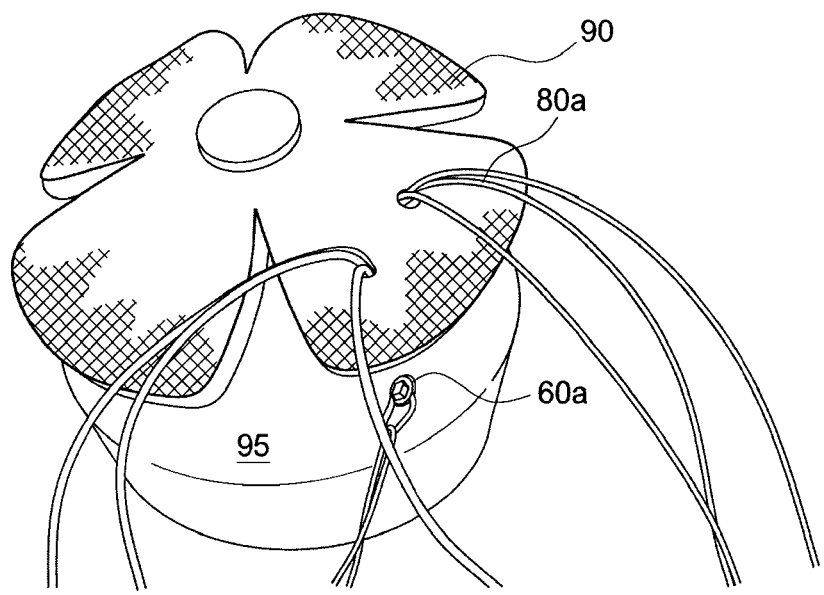
Figure 28:
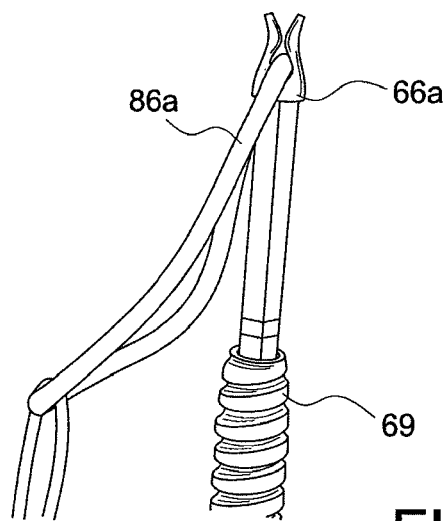
Figure 29:
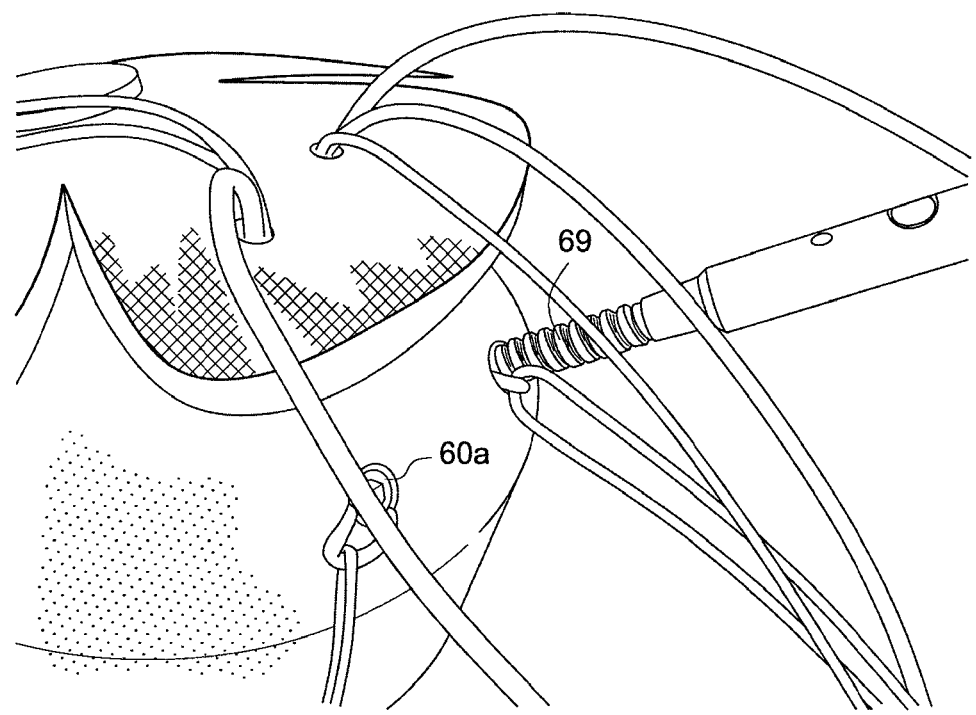
Figure 30:
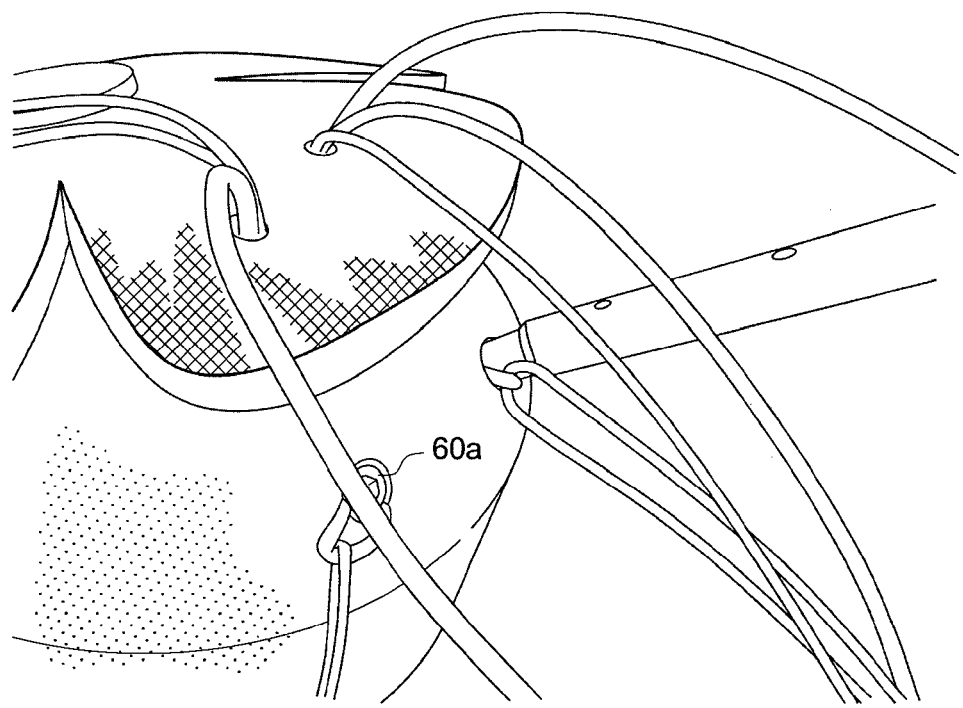
Figure 31:
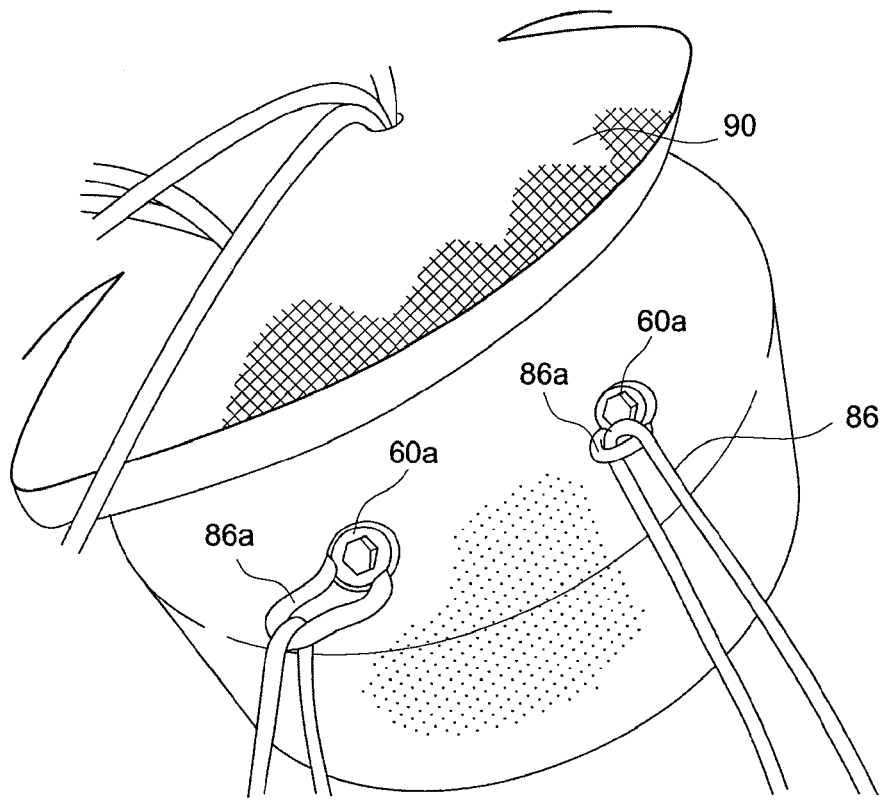
Figure 32:
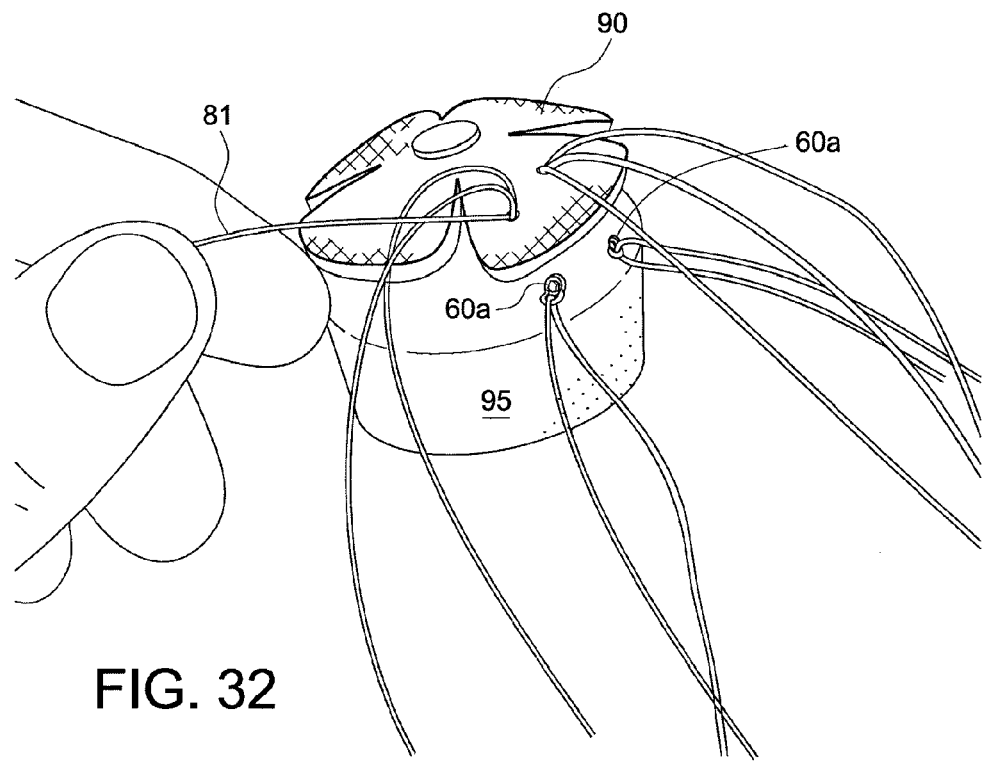
Figure 33:
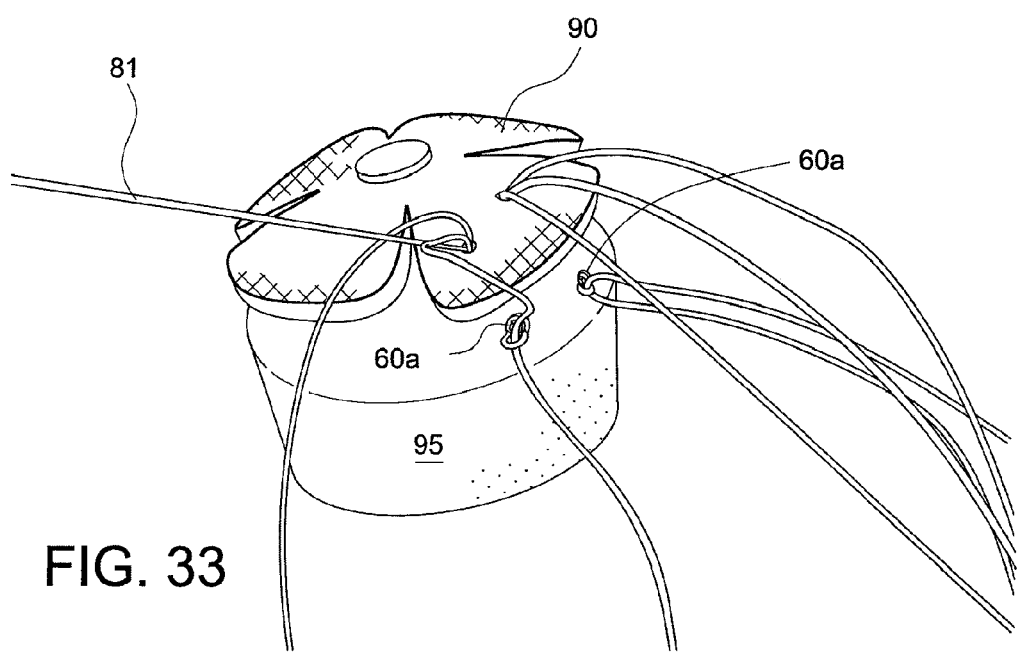
Figure 34:
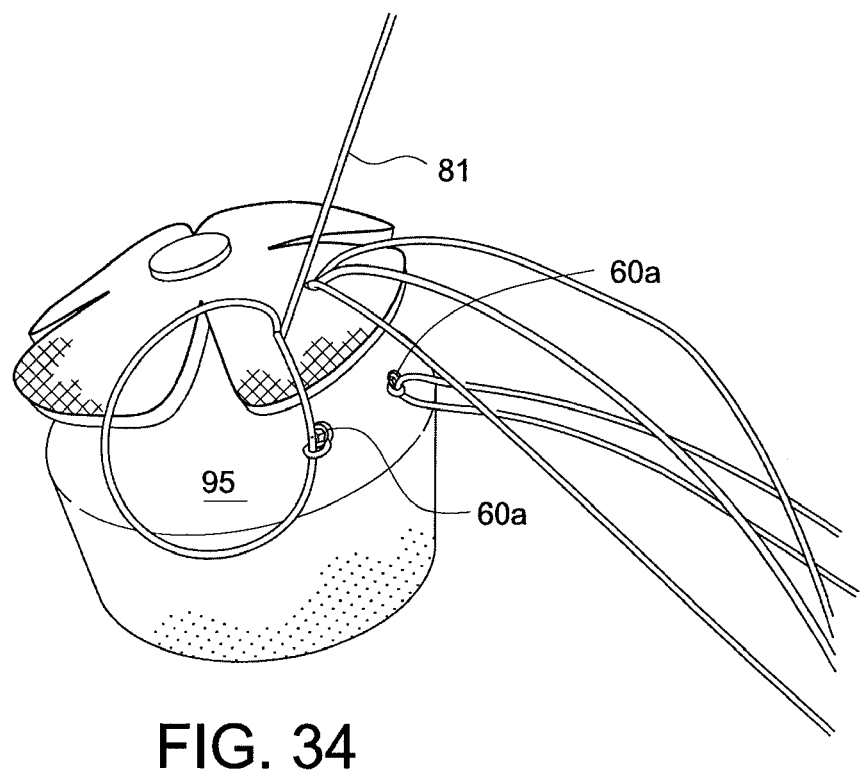
Figure 35:
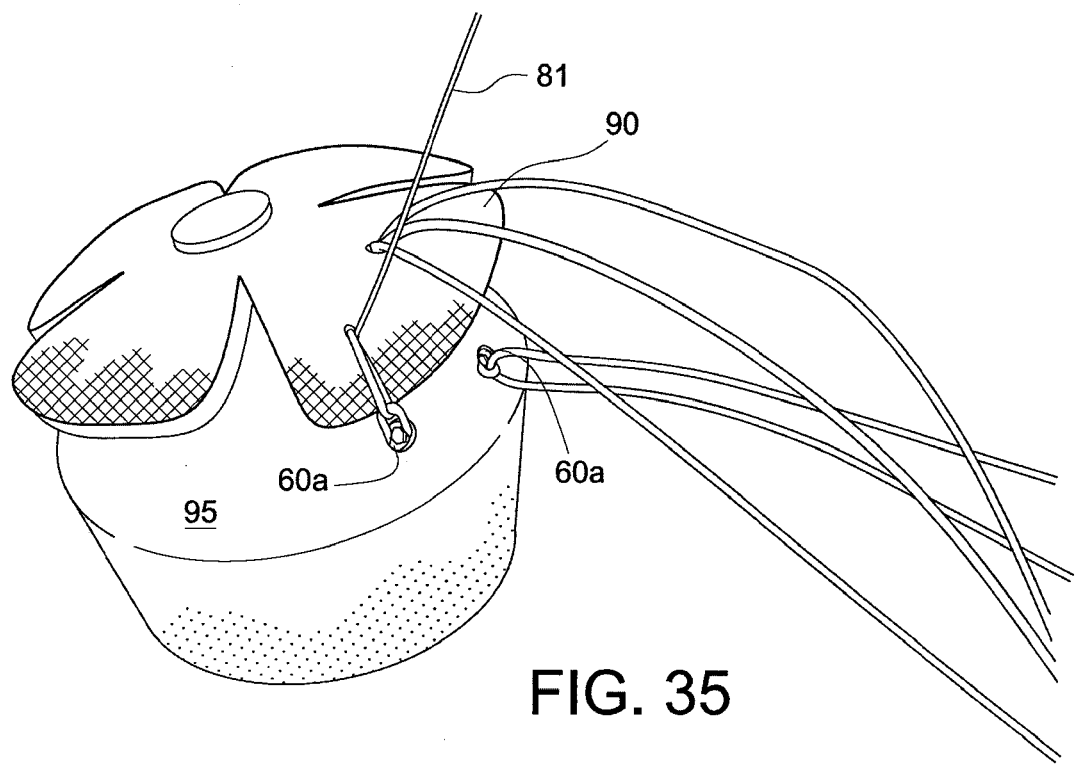

FIGS. 25-31 illustrate the insertion of another suture construct 80a with additional fixation devices such as anchors 50, 50a, 60, 60a. These steps are optional and may be repeated as necessary, depending on the characteristics of the specific surgical repair, for example, the extent of the damaged tissue to be repaired/affixed. Specifically, FIGS. 25-27 illustrate the insertion of another (second) fixation device 50a pre-loaded with a suture construct 80a. FIGS. 28-31 illustrate the fixation of loop 86a with a second fixation device 60a (attached to eyelet 66a of FIG. 28). FIG. 31 illustrates two fixation devices 60a for double row fixation of rotator cuff 90. Loops 86, 86a of knotless, tensionable construct 80a are attached to both fixation devices 50a, 60a and on each of the two parallel rows.

FIGS. 32-39 illustrate the tensioning of the knotless, tensionable construct 80a to achieve final construct 500 (FIG. 39) comprising double rows.

FIGS. 32-35: Pull cord 81 (free end 81) of the suture assembly 80a (of the first row) is grasped and pulled. Slack gets shuttled and reduces the size of the loop 86 via the splice in the modified Corkscrew® anchor 50a.

Figure 36:
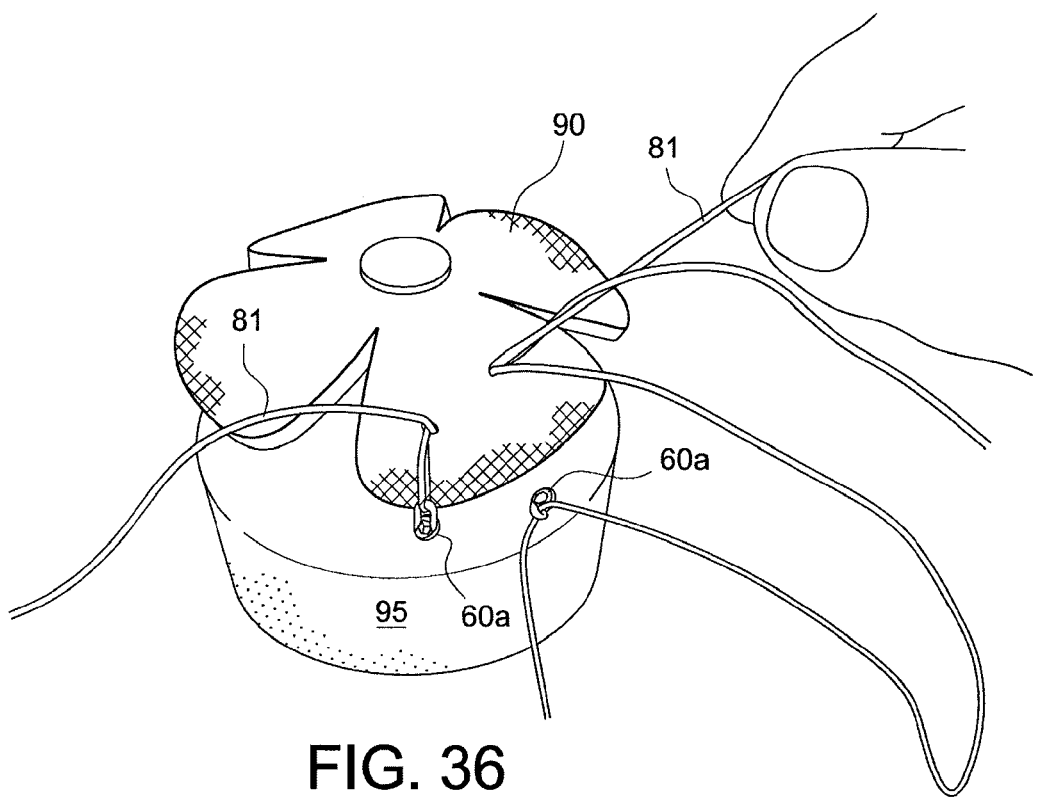
Figure 37:
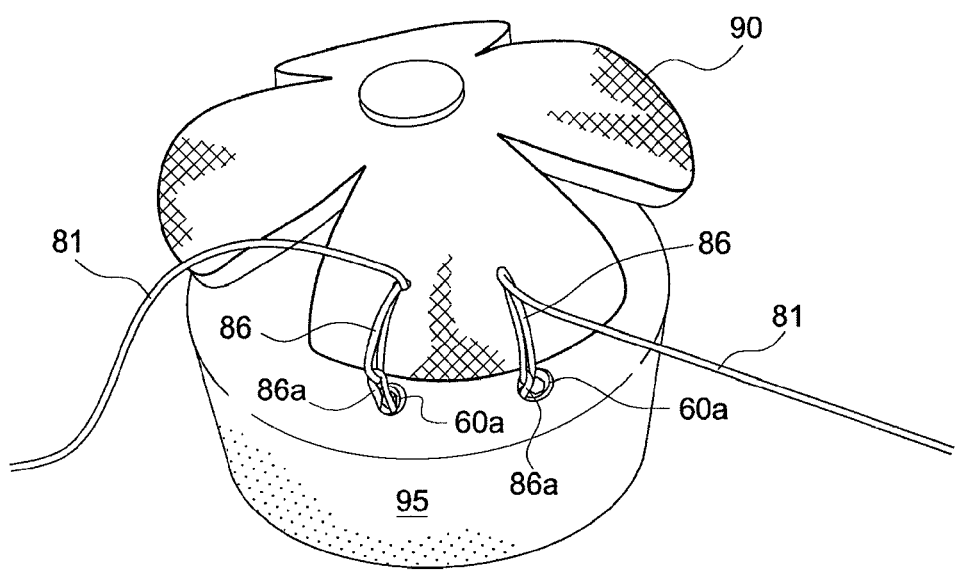
Figure 38:
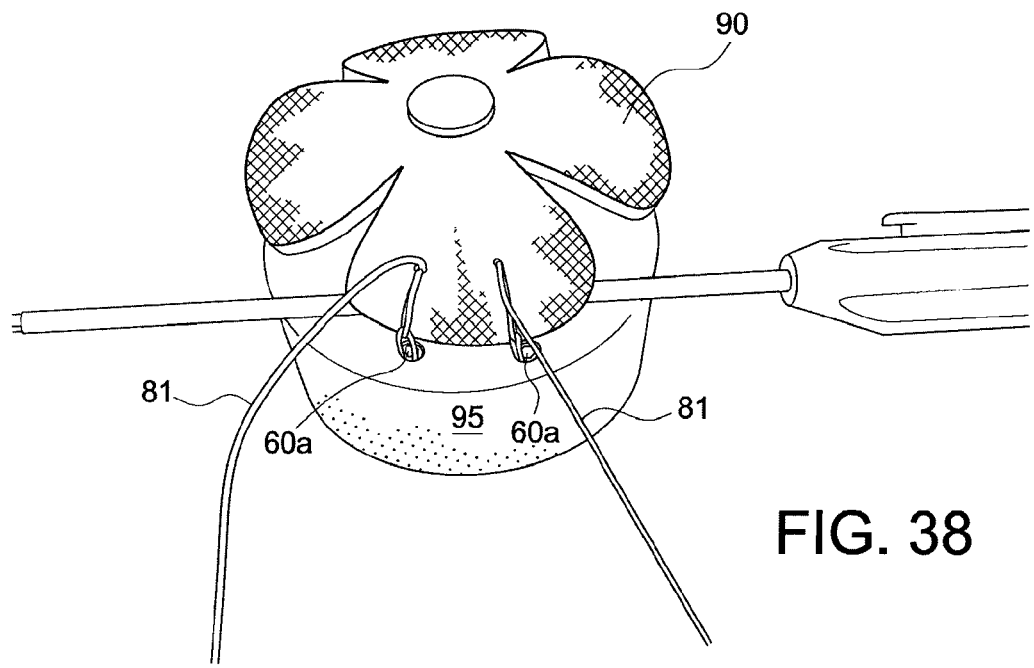

FIGS. 36-38: Pull cord 81 (free end 81) of the suture assembly 80a (of the second row) is grasped and pulled. Slack gets shuttled and pulled through the modified Corkscrew® anchor 50a.

Figure 39:
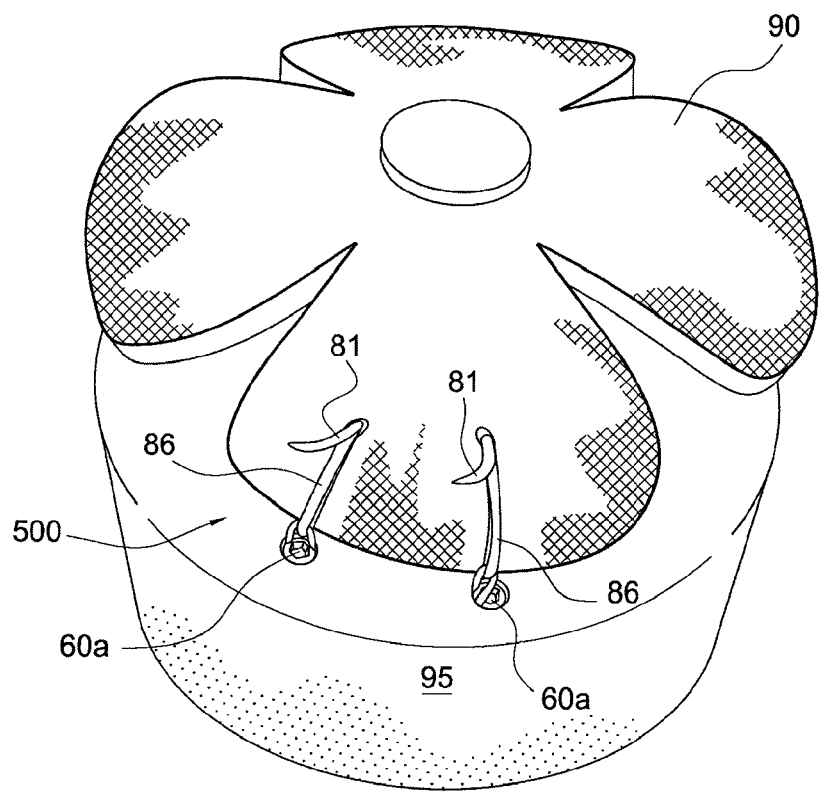

FIG. 39: Eventually all of slack is removed until the desired tension is reached and suture splice 85a and loops 86, 86a hold rotator cuff tissue 90 against bone 95. Excess suture is trimmed off and the steps are repeated as desired and for additional anchor fixation and multiple rows formation.

Anchor assembly 100, 200, 300, 400 with suture assembly 80, 80a, 80b, 80c attached to a plurality of knotless fixation devices 50, 50a, 60, 60a, 60b of the present invention may be employed for various repairs of soft tissue to bone (such as ligament, tendon or graft repairs, for example, rotator cuff and shoulder ligament repairs, Achilles tendon repairs, elbow repairs, among many others) that employ at least one knotless fixation device.

An exemplary method of attaching tissue to bone with surgical construct 200 of the present invention comprises inter alia the steps of: (i) providing a surgical construct 200 comprising a knotless fixation device 50a (for example, an anchor) pre-loaded with a tensionable construct 80a, the tensionable construct 80a consisting of a flexible strand 88 (for example, suture) extending through the body of the fixation device, the flexible strand comprising a knotted fixed end 82 (or an insert molded end), a free end 81, and a splice 85a with a spliced adjustable loop 86, the splice being located within the body of the fixation device and the spliced adjustable loop 86 having an adjustable length/perimeter, the splice 85 of the tensionable construct being pre-built with an additional attachment device or mechanism 86a (fixed loop 86a) attached to the spliced adjustable loop 86, the fixed loop 86a having a fixed perimeter; (ii) inserting the fixation device 50a (with the pre-assembled or pre-loaded construct 80a) into bone; (iii) passing the flexible strand 88 around or through tissue 90 to be fixated (or reattached) to bone 95; (iv) subsequently, attaching the fixed loop 86a to a distal open eyelet 66a of another fixation device 60a; (v) inserting the another fixation device 60a into bone 95; and (vi) pulling on the flexible strand 88 to reduce the perimeter of the spliced adjustable loop 86, to allow the soft tissue 90 to achieve the desired location relative to the bone 95 and to allow proper tensioning of the final construct 500.

Exemplary knotless anchors 50, 50a, 60, 60a, 60b may be formed of metal, biocompatible plastic such as PEEK or a bioabsorbable PLLA material. The anchors may be provided with a socket at the distal end (such as socket 19 of the anchor 50, 50a, 60, 60a, 60b) configured to securely engage a tip of a driver. The socket of the anchor may have any shape adapted to receive a driver tip for pushing the anchors, for example, tap-in or screw-in style anchors. Tensionable knotless anchors 50, 50a, 60, 60a, 60b may be made of one or more pieces, or may be provided as integrated devices.

The knotless suture constructs and systems of the present invention are used in conjunction with any knotless fixation devices which are pre-loaded with a flexible strand forming a splice within or outside the body of the fixation device. The fixation devices may be any of swivel and/or screw-in suture anchors and/or push-in suture anchors (such as an Arthrex SwiveLock® anchor, disclosed in U.S. Patent Application Publication No. 2008/0004659 or a PushLock® anchor, as disclosed in U.S. Pat. No. 7,329,272). The fixation devices may be also any anchors, implants or screws (such as interference screws or tenodesis screws) or any fixation element that allows attachment/fixation of the knotless suture construct to bone. The fixation devices/implants may have various sizes (various diameters and/or lengths) and may be formed of biocompatible materials such as PEEK, biocomposite materials, metals and/or metal alloys, or combination of such materials, among others. The fixation devices may be unitary or may be multiple-piece constructs.

The flexible strand 88 may be a high-strength suture, such as an ultrahigh molecular weight polyethylene (UHMWPE) suture without a core which is the preferred material as this material allows easy splicing. Alternatively, the high strength suture may be a FiberWire® suture, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra (Honeywell) and Dyneema (DSM) fibers, braided with at least one other fiber, natural or synthetic, to form lengths of suture material.

The strands may also be formed of a stiff material, or combination of stiff and flexible materials, depending on the intended application. The strands may be also coated and/or provided in different colors. The knotless anchors of the present invention can be used with any type of flexible material or suture that forms a splice and a loop.

The knotless suture constructs also include sutures that are spliced—at least in part—in a manner similar to an Arthrex ACL TightRope®, such as disclosed in U.S. Patent Application Publication Nos. 2010/0256677 and 2010/0268273, the disclosures of which are incorporated by reference herein.

The anchor assembly of the present invention advantageously minimizes suture handling and management. The use of knotless anchors (such as push-in or screw-in type anchors) also provides secure fixation of the suture construct—the secure suture construct results from the suture being pushed into a hole and held tightly by anchors. The suture assembly employed in conjunction with the knotless anchors also allows for knotless tensioning of the tissue (rotator cuff) after the plurality of knotless anchors have been implanted.

In the embodiments detailed above, suture is used with the knotless anchors to fix tissue to bone. However, the knotless anchors of the present invention can be used with any type of flexible material or suture that forms a splice and a loop. In yet additional embodiments, any combination of suture and suture tape may be employed, depending on the characteristics of the specific surgical repair and/or as desired.

While the present invention is described herein with reference to illustrative embodiments for particular applications, it should be understood that the invention is not limited thereto. Those having ordinary skill in the art and access to the teachings provided herein will recognize additional modifications, applications, embodiments and substitution of equivalents all fall within the scope of the invention. Accordingly, the invention is to be limited not by the specific disclosure herein, but only by the appended claims.

What is claimed is:

1. A surgical construct for tissue repairs, comprising:
   a first fixation device comprising a body with a cannulation, a longitudinal axis, a proximal end and a distal end, the cannulation extending in a direction parallel to the longitudinal axis; and
   a self-locking tensionable construct pre-loaded on the first fixation device, the tensionable construct consisting of a flexible strand having a free end and a static knot located at the distal end of the first fixation device, a splice, a first loop, and a second loop attached to the first loop, wherein the tensionable construct extends through the cannulation of the first fixation device, wherein the splice is located entirely within the body of the first fixation device, and wherein the first loop has an adjustable length and the second loop has a fixed length, and wherein the first loop and the second loop extend away from and above the proximal end of the first fixation device.

2. The surgical construct of claim 1, further comprising a second fixation device attached to the second loop.

3. The surgical construct of claim 2, wherein the second loop is attached to an open distal eyelet of the second fixation device.

4. A tissue repair system for attachment of tissue to bone, comprising:
   a first tensionable suture construct extending between a first plurality of fixation devices, the first tensionable suture construct including a first suture loop and a second suture loop attached to the first suture loop, a splice located within a body of a first fixation device of the first plurality of fixation devices, and a free suture end,
   wherein the first tensionable suture construct extends through a cannulation of the first fixation device, and wherein at least a portion of the first suture loop and at least a portion of the second suture loop extend above tissue and above bone, and wherein the second suture loop is attached to an open distal end of a second fixation device of the first plurality of fixation devices, wherein the tissue repair system further comprises a second tensionable suture construct extending between a second plurality of fixation devices, the second tensionable suture construct including a first suture loop and a second suture loop attached to the first suture loop, a splice located within a body of a first fixation device of the second plurality of fixation devices, and a free suture end extending above tissue, and wherein the second suture loop is attached to an open distal end of a second fixation device of the second plurality of fixation devices.

5. The tissue repair system of claim 4, wherein the first loop has an adjustable perimeter and the second loop has a fixed perimeter.

6. The tissue repair system of claim 4, wherein the repair is a knotless double row rotator cuff repair.

* * * * *